US012788777B2

(12) United States Patent
De Waziers et al.

(10) Patent No.: US 12,788,777 B2
(45) Date of Patent: Nov. 10, 2026

(54) GENETICALLY MODIFIED HUMAN STEM CELL EXPRESSING A MUTANT HUMAN CYTOCHROME P450 2B6 PROTEIN AND USE THEREOF IN THE TREATMENT OF CANCER

(71) Applicants: ASSISTANCE PUBLIQUE-HOPITAUX DE PARIS, Paris (FR); UNIVERSITE PARIS CITE, Paris (FR); INSTITUT NATIONAL DE LA SANTE ET DE LA RECHERCHE MEDICALE (INSERM), Paris (FR); SORBONNE UNIVERSITE, Paris (FR)

(72) Inventors: Isabelle De Waziers, Paris (FR); Philippe Beaune, Paris (FR); Marc Sapoval, Arcueil (FR); Olivier Pellerin, Paris (FR); Benjamin Nayagom, Saone (FR)

(73) Assignees: ASSISTANCE PUBLIQUE-HOPITAUX DE PARIS, Paris (FR); UNIVERSITE PARIS CITE, Paris (FR); INSTITUT NATIONAL DE LA SANTE ET DE LA RECHERCHE MEDICALE, Paris (FR); SORBONNE UNIVERSITE, Paris (FR)

( * ) Notice: Subject to any disclaimer, the term of this patent is extended or adjusted under 35 U.S.C. 154(b) by 1249 days.

(21) Appl. No.: 17/768,016

(22) PCT Filed: Oct. 13, 2020

(86) PCT No.: PCT/EP2020/078806

§ 371 (c)(1),
(2) Date: Apr. 11, 2022

(87) PCT Pub. No.: WO2021/074167

PCT Pub. Date: Apr. 22, 2021

(65) Prior Publication Data

US 2022/0409668 A1 Dec. 29, 2022

(30) Foreign Application Priority Data

Oct. 14, 2019 (FR) .................................. FR1911386

(51) Int. Cl.

*A61K 35/28* (2015.01)
*A61K 45/06* (2006.01)
*C12N 5/0775* (2010.01)
*C12N 9/02* (2006.01)

(52) U.S. Cl.

CPC .............. *A61K 35/28* (2013.01); *A61K 45/06* (2013.01); *C12N 5/0663* (2013.01); *C12N 9/0042* (2013.01); *C12Y 106/02004* (2013.01); *C07K 2319/00* (2013.01); *C12N 2510/00* (2013.01)

(58) Field of Classification Search

None
See application file for complete search history.

(56) References Cited

U.S. PATENT DOCUMENTS

| | | | | |
|---|---|---|---|---|
| 9,243,231 | B2 * | 1/2016 | De Waziers | C12N 9/0042 |
| 10,030,233 | B2 * | 7/2018 | Chaudhuri | C12N 9/0042 |

FOREIGN PATENT DOCUMENTS

WO 2012/150326 A1 11/2012

OTHER PUBLICATIONS

Amara Ikrame et al: Mesenchymal stem 1cells as cellular vehicles for prodrug gene therapy against tumors, Biochimie, Masson, Paris, FR, vol. 105, Jun. 27, 2014 (Jun. 27, 2014), pp. 4-11.

Stefan Pellenz et al: New Human Chromosomal Sites with “Safe Harbor” Potential for Targeted Transgene Insertion, Human Gene Therapy, DOI: 10.1089/hum.2018.169, Mar. 28, 2019, pp. 1-15.

Eirini P Papapetrou et al.: Gene Insertion Into Genomic Safe Harbors for Human Gene Therapy, Molecular Therapy : The Journal of the American Society of Gene Therapy, vol. 24, No. 4, Apr. 1, 2016, pp. 678-684.

Natalia Gomez-Ospina et al. “Human genome-edited hematopoietic stem cells phenotypically correct Mucopolysaccharidosis type I” Nature Communications, vol. 10, No. 1, pp. 1-14, Sep. 6, 2019.

Yasuyoshi Kimura et al. “Human Genomic Safe Harbors and the Suicide Gene-Based Safeguard System for PSC-Based Cell Therapy” Stem Cells Translational Medicine, US, vol. 8, No. 7, Mar. 19, 2019, pp. 627-638.

Roy Pet al. “Activation of oxazaphosphorines by cytochrome P450: Application to gene-directed enzyme prodrug therapy for cancer” Toxicology in Vitro, Elsevier Science, GB, vol. 20, No. 2, Mar. 1, 2006, pp. 176-186.

* cited by examiner

*Primary Examiner* — Blaine Lankford
(74) *Attorney, Agent, or Firm* — Arrigo, Lee, Guttman & Mouta-Bellum LLP

(57) ABSTRACT

The present invention relates to a genetically modified human stem cell, in which said human stem cell comprises an exogenous nucleic acid comprising a region coding for a fusion protein comprising a mutant human cytochrome P450 2B6 (CYP2B6*) protein of SEQ ID No. 1 or a variant or fragment thereof and an NADPH-cytochrome P450 reductase protein of SEQ ID No. 2 or a variant or fragment thereof, functionally bound to a promoter, said exogenous nucleic acid having been integrated into one of the genomic safe harbors of said human stem cell. The invention also relates to the use of said cell for the treatment of cancer and/or cancer recurrences and/or associated metastases, particularly the solid tumours, and in particular the hepatocellular carcinomas and/or associated metastases.

21 Claims, No Drawings

Specification includes a Sequence Listing.

SEQUENCE LISTING

<160> NUMBER OF SEQ ID NOS: 8

<210> SEQ ID NO 1
<211> LENGTH: 491
<212> TYPE: PRT
<213> ORGANISM: Homo sapiens

<400> SEQUENCE: 1

Met Glu Leu Ser Val Leu Leu Phe Leu Ala Leu Leu Thr Gly Leu Leu
1 5 10 15

Leu Leu Leu Val Gln Arg His Pro Asn Thr His Asp Arg Leu Pro Pro
20 25 30

Gly Pro Arg Pro Leu Pro Leu Leu Gly Asn Leu Leu Gln Met Asp Arg
35 40 45

Arg Gly Leu Leu Lys Ser Phe Leu Arg Phe Arg Glu Lys Tyr Gly Asp
50 55 60

Val Phe Thr Val His Leu Gly Pro Arg Pro Val Val Met Leu Cys Gly
65 70 75 80

Val Glu Ala Ile Arg Glu Ala Leu Val Asp Lys Ala Glu Ala Phe Ser
85 90 95

Gly Arg Gly Lys Ile Ala Met Val Asp Pro Phe Phe Arg Gly Tyr Gly
100 105 110

Val Val Phe Ala Asn Gly Asn Arg Trp Lys Val Leu Arg Arg Phe Ser
115 120 125

Val Thr Thr Met Arg Asp Phe Gly Met Gly Lys Arg Ser Val Glu Glu
130 135 140

Arg Ile Gln Glu Glu Ala Gln Cys Leu Ile Glu Glu Leu Arg Lys Ser
145 150 155 160

Lys Gly Ala Leu Met Asp Pro Thr Phe Leu Phe Gln Ser Ile Thr Ala
165 170 175

Asn Ile Ile Cys Ser Ile Val Phe Gly Lys Arg Phe His Tyr Gln Asp
180 185 190

Gln Glu Phe Leu Lys Met Met Asn Leu Phe Tyr Gln Thr Phe Ser Leu
195 200 205

Ile Ser Ser Val Phe Gly Gln Leu Phe Glu Leu Phe Ser Gly Phe Leu
210 215 220

Lys Tyr Phe Pro Gly Ala His Arg Gln Val Tyr Lys Asn Leu Gln Glu
225 230 235 240

Ile Asn Ala Tyr Ile Gly His Ser Val Glu Lys His Arg Glu Thr Leu
245 250 255

Asp Pro Ser Ala Pro Lys Asp Leu Ile Asp Thr Tyr Leu Leu His Met
260 265 270

Glu Lys Glu Lys Ser Asn Ala His Ser Glu Phe Ser His Gln Asn Leu
275 280 285

Asn Leu Asn Thr Leu Ser Leu Phe Phe Ala Gly Thr Glu Thr Thr Ser
290 295 300

Thr Thr Leu Arg Tyr Gly Phe Leu Leu Met Leu Lys Tyr Pro His Val
305 310 315 320

Ala Glu Arg Val Tyr Arg Glu Ile Glu Gln Val Ile Gly Pro His Arg
325 330 335

Pro Pro Glu Leu His Asp Arg Ala Lys Met Pro Tyr Thr Glu Ala Val
340 345 350

Ile Tyr Glu Ile Gln Arg Phe Ser Asp Leu Leu Pro Met Gly Val Pro
355 360 365

```
His Ile Val Thr Gln His Thr Ser Phe Arg Gly Tyr Ile Ile Pro Lys
    370                 375                 380

Asp Thr Glu Val Phe Leu Ile Leu Ser Thr Ala Leu His Asp Pro His
385                 390                 395                 400

Tyr Phe Glu Lys Pro Asp Ala Phe Asn Pro Asp His Phe Leu Asp Ala
                405                 410                 415

Asn Gly Ala Leu Lys Lys Thr Glu Ala Phe Ile Pro Phe Ser Leu Gly
            420                 425                 430

Lys Arg Ile Cys Leu Gly Glu Gly Ile Ala Arg Ala Glu Leu Phe Leu
        435                 440                 445

Phe Phe Thr Thr Ile Leu Gln Asn Phe Ser Met Ala Ser Pro Val Ala
    450                 455                 460

Pro Glu Asp Ile Asp Leu Thr Pro Gln Glu Cys Gly Trp Gly Lys Ile
465                 470                 475                 480

Pro Pro Thr Tyr Gln Ile Arg Phe Leu Pro Arg
                485                 490


<210> SEQ ID NO 2
<211> LENGTH: 621
<212> TYPE: PRT
<213> ORGANISM: Homo sapiens

<400> SEQUENCE: 2

Ile Gln Thr Leu Thr Ser Ser Val Arg Glu Ser Ser Phe Val Glu Lys
1               5                   10                  15

Met Lys Lys Thr Gly Arg Asn Ile Ile Val Phe Tyr Gly Ser Gln Thr
            20                  25                  30

Gly Thr Ala Glu Glu Phe Ala Asn Arg Leu Ser Lys Asp Ala His Arg
        35                  40                  45

Tyr Gly Met Arg Gly Met Ser Ala Asp Pro Glu Glu Tyr Asp Leu Ala
    50                  55                  60

Asp Leu Ser Ser Leu Pro Glu Ile Asp Asn Ala Leu Val Val Phe Cys
65                  70                  75                  80

Met Ala Thr Tyr Gly Glu Gly Asp Pro Thr Asp Asn Ala Gln Asp Phe
                85                  90                  95

Tyr Asp Trp Leu Gln Glu Thr Asp Val Asp Leu Ser Gly Val Lys Phe
            100                 105                 110

Ala Val Phe Gly Leu Gly Asn Lys Thr Tyr Glu His Phe Asn Ala Met
        115                 120                 125

Gly Lys Tyr Val Asp Lys Arg Leu Glu Gln Leu Gly Ala Gln Arg Ile
    130                 135                 140

Phe Glu Leu Gly Leu Gly Asp Asp Asp Gly Asn Leu Glu Glu Asp Phe
145                 150                 155                 160

Ile Thr Trp Arg Glu Gln Phe Trp Pro Ala Val Cys Glu His Phe Gly
                165                 170                 175

Val Glu Ala Thr Gly Glu Glu Ser Ser Ile Arg Gln Tyr Glu Leu Val
            180                 185                 190

Val His Thr Asp Ile Asp Ala Ala Lys Val Tyr Met Gly Glu Met Gly
        195                 200                 205

Arg Leu Lys Ser Tyr Glu Asn Gln Lys Pro Pro Phe Asp Ala Lys Asn
    210                 215                 220

Pro Phe Leu Ala Ala Val Thr Thr Asn Arg Lys Leu Asn Gln Gly Thr
225                 230                 235                 240

Glu Arg His Leu Met His Leu Glu Leu Asp Ile Ser Asp Ser Lys Ile
                245                 250                 255
```

```
Arg Tyr Glu Ser Gly Asp His Val Ala Val Tyr Pro Ala Asn Asp Ser
            260                 265                 270

Ala Leu Val Asn Gln Leu Gly Lys Ile Leu Gly Ala Asp Leu Asp Val
        275                 280                 285

Val Met Ser Leu Asn Asn Leu Asp Glu Glu Ser Asn Lys Lys His Pro
    290                 295                 300

Phe Pro Cys Pro Thr Ser Tyr Arg Thr Ala Leu Thr Tyr Tyr Leu Asp
305                 310                 315                 320

Ile Thr Asn Pro Pro Arg Thr Asn Val Leu Tyr Glu Leu Ala Gln Tyr
                325                 330                 335

Ala Ser Glu Pro Ser Glu Gln Glu Leu Leu Arg Lys Met Ala Ser Ser
            340                 345                 350

Ser Gly Glu Gly Lys Glu Leu Tyr Leu Ser Trp Val Val Glu Ala Arg
        355                 360                 365

Arg His Ile Leu Ala Ile Leu Gln Asp Cys Pro Ser Leu Arg Pro Pro
    370                 375                 380

Ile Asp His Leu Cys Glu Leu Leu Pro Arg Leu Gln Ala Arg Tyr Tyr
385                 390                 395                 400

Ser Ile Ala Ser Ser Ser Lys Val His Pro Asn Ser Val His Ile Cys
                405                 410                 415

Ala Val Val Val Glu Tyr Glu Thr Lys Ala Gly Arg Ile Asn Lys Gly
            420                 425                 430

Val Ala Thr Asn Trp Leu Arg Ala Lys Glu Pro Ala Gly Glu Asn Gly
        435                 440                 445

Gly Arg Ala Leu Val Pro Met Phe Val Arg Lys Ser Gln Phe Arg Leu
    450                 455                 460

Pro Phe Lys Ala Thr Thr Pro Val Ile Met Val Gly Pro Gly Thr Gly
465                 470                 475                 480

Val Ala Pro Phe Ile Gly Phe Ile Gln Glu Arg Ala Trp Leu Arg Gln
                485                 490                 495

Gln Gly Lys Glu Val Gly Glu Thr Leu Leu Tyr Tyr Gly Cys Arg Arg
            500                 505                 510

Ser Asp Glu Asp Tyr Leu Tyr Arg Glu Glu Leu Ala Gln Phe His Arg
        515                 520                 525

Asp Gly Ala Leu Thr Gln Leu Asn Val Ala Phe Ser Arg Glu Gln Ser
    530                 535                 540

His Lys Val Tyr Val Gln His Leu Leu Lys Gln Asp Arg Glu His Leu
545                 550                 555                 560

Trp Lys Leu Ile Glu Gly Gly Ala His Ile Tyr Val Cys Gly Asp Ala
                565                 570                 575

Arg Asn Met Ala Arg Asp Val Gln Asn Thr Phe Tyr Asp Ile Val Ala
            580                 585                 590

Glu Leu Gly Ala Met Glu His Ala Gln Ala Val Asp Tyr Ile Lys Lys
        595                 600                 605

Leu Met Thr Lys Gly Arg Tyr Ser Leu Asp Val Trp Ser
    610                 615                 620
```

<210> SEQ ID NO 3
<211> LENGTH: 491
<212> TYPE: PRT
<213> ORGANISM: Homo sapiens

<400> SEQUENCE: 3

```
Met Glu Leu Ser Val Leu Leu Phe Leu Ala Leu Leu Thr Gly Leu Leu
```

-continued

```
1               5                   10                  15

Leu Leu Leu Val Gln Arg His Pro Asn Thr His Asp Arg Leu Pro Pro
            20                  25                  30

Gly Pro Arg Pro Leu Pro Leu Leu Gly Asn Leu Leu Gln Met Asp Arg
        35                  40                  45

Arg Gly Leu Leu Lys Ser Phe Leu Arg Phe Arg Glu Lys Tyr Gly Asp
    50                  55                  60

Val Phe Thr Val His Leu Gly Pro Arg Pro Val Val Met Leu Cys Gly
65                  70                  75                  80

Val Glu Ala Ile Arg Glu Ala Leu Val Asp Lys Ala Glu Ala Phe Ser
                85                  90                  95

Gly Arg Gly Lys Ile Ala Met Val Asp Pro Phe Phe Arg Gly Tyr Gly
            100                 105                 110

Val Ile Phe Ala Asn Gly Asn Arg Trp Lys Val Leu Arg Arg Phe Ser
        115                 120                 125

Val Thr Thr Met Arg Asp Phe Gly Met Gly Lys Arg Ser Val Glu Glu
    130                 135                 140

Arg Ile Gln Glu Glu Ala Gln Cys Leu Ile Glu Glu Leu Arg Lys Ser
145                 150                 155                 160

Lys Gly Ala Leu Met Asp Pro Thr Phe Leu Phe Gln Ser Ile Thr Ala
                165                 170                 175

Asn Ile Ile Cys Ser Ile Val Phe Gly Lys Arg Phe His Tyr Gln Asp
            180                 185                 190

Gln Glu Phe Leu Lys Met Leu Asn Leu Phe Tyr Gln Thr Phe Ser Leu
        195                 200                 205

Ile Ser Ser Val Phe Gly Gln Leu Phe Glu Leu Phe Ser Gly Phe Leu
    210                 215                 220

Lys Tyr Phe Pro Gly Ala His Arg Gln Val Tyr Lys Asn Leu Gln Glu
225                 230                 235                 240

Ile Asn Ala Tyr Ile Gly His Ser Val Glu Lys His Arg Glu Thr Leu
                245                 250                 255

Asp Pro Ser Ala Pro Lys Asp Leu Ile Asp Thr Tyr Leu Leu His Met
            260                 265                 270

Glu Lys Glu Lys Ser Asn Ala His Ser Glu Phe Ser His Gln Asn Leu
        275                 280                 285

Asn Leu Asn Thr Leu Ser Leu Phe Phe Ala Gly Thr Glu Thr Thr Ser
    290                 295                 300

Thr Thr Leu Arg Tyr Gly Phe Leu Leu Met Leu Lys Tyr Pro His Val
305                 310                 315                 320

Ala Glu Arg Val Tyr Arg Glu Ile Glu Gln Val Ile Gly Pro His Arg
                325                 330                 335

Pro Pro Glu Leu His Asp Arg Ala Lys Met Pro Tyr Thr Glu Ala Val
            340                 345                 350

Ile Tyr Glu Ile Gln Arg Phe Ser Asp Leu Leu Pro Met Gly Val Pro
        355                 360                 365

His Ile Val Thr Gln His Thr Ser Phe Arg Gly Tyr Ile Ile Pro Lys
    370                 375                 380

Asp Thr Glu Val Phe Leu Ile Leu Ser Thr Ala Leu His Asp Pro His
385                 390                 395                 400

Tyr Phe Glu Lys Pro Asp Ala Phe Asn Pro Asp His Phe Leu Asp Ala
                405                 410                 415

Asn Gly Ala Leu Lys Lys Thr Glu Ala Phe Ile Pro Phe Ser Leu Gly
            420                 425                 430
```

```
Lys Arg Ile Cys Leu Gly Glu Gly Ile Ala Arg Ala Glu Leu Phe Leu
        435                 440                 445

Phe Phe Thr Thr Ile Leu Gln Asn Phe Ser Met Ala Ser Pro Val Ala
    450                 455                 460

Pro Glu Asp Ile Asp Leu Thr Pro Gln Glu Cys Gly Val Gly Lys Ile
465                 470                 475                 480

Pro Pro Thr Tyr Gln Ile Arg Phe Leu Pro Arg
                485                 490


<210> SEQ ID NO 4
<211> LENGTH: 1464
<212> TYPE: PRT
<213> ORGANISM: Homo sapiens

<400> SEQUENCE: 4

Met Glu Leu Ser Val Leu Leu Phe Leu Ala Leu Leu Thr Gly Leu Leu
1               5                   10                  15

Leu Leu Leu Val Gln Arg His Pro Asn Thr His Asp Arg Leu Pro Pro
            20                  25                  30

Gly Pro Arg Pro Leu Pro Leu Leu Gly Asn Leu Leu Gln Met Asp Arg
        35                  40                  45

Arg Gly Leu Leu Lys Ser Phe Leu Arg Phe Arg Glu Lys Tyr Gly Asp
    50                  55                  60

Val Phe Thr Val His Leu Gly Pro Arg Pro Val Val Met Leu Cys Gly
65                  70                  75                  80

Val Glu Ala Ile Arg Glu Ala Leu Val Asp Lys Ala Glu Ala Phe Ser
                85                  90                  95

Gly Arg Gly Lys Ile Ala Met Val Asp Pro Phe Phe Arg Gly Tyr Gly
            100                 105                 110

Val Val Phe Ala Asn Gly Asn Arg Trp Lys Val Leu Arg Arg Phe Ser
        115                 120                 125

Val Thr Thr Met Arg Asp Phe Gly Met Gly Lys Arg Ser Val Glu Glu
    130                 135                 140

Arg Ile Gln Glu Glu Ala Gln Cys Leu Ile Glu Glu Leu Arg Lys Ser
145                 150                 155                 160

Lys Gly Ala Leu Met Asp Pro Thr Phe Leu Phe Gln Ser Ile Thr Ala
                165                 170                 175

Asn Ile Ile Cys Ser Ile Val Phe Gly Lys Arg Phe His Tyr Gln Asp
            180                 185                 190

Gln Glu Phe Leu Lys Met Met Asn Leu Phe Tyr Gln Thr Phe Ser Leu
        195                 200                 205

Ile Ser Ser Val Phe Gly Gln Leu Phe Glu Leu Phe Ser Gly Phe Leu
    210                 215                 220

Lys Tyr Phe Pro Gly Ala His Arg Gln Val Tyr Lys Asn Leu Gln Glu
225                 230                 235                 240

Ile Asn Ala Tyr Ile Gly His Ser Val Glu Lys His Arg Glu Thr Leu
                245                 250                 255

Asp Pro Ser Ala Pro Lys Asp Leu Ile Asp Thr Tyr Leu Leu His Met
            260                 265                 270

Glu Lys Glu Lys Ser Asn Ala His Ser Glu Phe Ser His Gln Asn Leu
        275                 280                 285

Asn Leu Asn Thr Leu Ser Leu Phe Phe Ala Gly Thr Glu Thr Thr Ser
    290                 295                 300

Thr Thr Leu Arg Tyr Gly Phe Leu Leu Met Leu Lys Tyr Pro His Val
```

```
305                 310                 315                 320

Ala Glu Arg Val Tyr Arg Glu Ile Glu Gln Val Ile Gly Pro His Arg
                325                 330                 335

Pro Pro Glu Leu His Asp Arg Ala Lys Met Pro Tyr Thr Glu Ala Val
            340                 345                 350

Ile Tyr Glu Ile Gln Arg Phe Ser Asp Leu Leu Pro Met Gly Val Pro
        355                 360                 365

His Ile Val Thr Gln His Thr Ser Phe Arg Gly Tyr Ile Ile Pro Lys
    370                 375                 380

Asp Thr Glu Val Phe Leu Ile Leu Ser Thr Ala Leu His Asp Pro His
385                 390                 395                 400

Tyr Phe Glu Lys Pro Asp Ala Phe Asn Pro Asp His Phe Leu Asp Ala
                405                 410                 415

Asn Gly Ala Leu Lys Lys Thr Glu Ala Phe Ile Pro Phe Ser Leu Gly
            420                 425                 430

Lys Arg Ile Cys Leu Gly Glu Gly Ile Ala Arg Ala Glu Leu Phe Leu
        435                 440                 445

Phe Phe Thr Thr Ile Leu Gln Asn Phe Ser Met Ala Ser Pro Val Ala
    450                 455                 460

Pro Glu Asp Ile Asp Leu Thr Pro Gln Glu Cys Gly Trp Gly Lys Ile
465                 470                 475                 480

Pro Pro Thr Tyr Gln Ile Arg Phe Leu Pro Arg Ser Ser Ser Thr Ile
                485                 490                 495

Gln Thr Leu Thr Ser Ser Val Arg Glu Ser Ser Phe Val Glu Lys Met
            500                 505                 510

Lys Lys Thr Gly Arg Asn Ile Ile Val Phe Tyr Gly Ser Gln Thr Gly
        515                 520                 525

Thr Ala Glu Glu Phe Ala Asn Arg Leu Ser Lys Asp Ala His Arg Tyr
    530                 535                 540

Gly Met Arg Gly Met Ser Ala Asp Pro Glu Glu Tyr Asp Leu Ala Asp
545                 550                 555                 560

Leu Ser Ser Leu Pro Glu Ile Asp Asn Ala Leu Val Val Phe Cys Met
                565                 570                 575

Ala Thr Tyr Gly Glu Gly Asp Pro Thr Asp Asn Ala Gln Asp Phe Tyr
            580                 585                 590

Asp Trp Leu Gln Glu Thr Asp Val Asp Leu Ser Gly Val Lys Phe Ala
        595                 600                 605

Val Phe Gly Leu Gly Asn Lys Thr Tyr Glu His Phe Asn Ala Met Gly
    610                 615                 620

Lys Tyr Val Asp Lys Arg Leu Glu Gln Leu Gly Ala Gln Arg Ile Phe
625                 630                 635                 640

Glu Leu Gly Leu Gly Asp Asp Asp Gly Asn Leu Glu Glu Asp Phe Ile
                645                 650                 655

Thr Trp Arg Glu Gln Phe Trp Pro Ala Val Cys Glu His Phe Gly Val
            660                 665                 670

Glu Ala Thr Gly Glu Glu Ser Ser Ile Arg Gln Tyr Glu Leu Val Val
        675                 680                 685

His Thr Asp Ile Asp Ala Ala Lys Val Tyr Met Gly Glu Met Gly Arg
    690                 695                 700

Leu Lys Ser Tyr Glu Asn Gln Lys Pro Pro Phe Asp Ala Lys Asn Pro
705                 710                 715                 720

Phe Leu Ala Ala Val Thr Thr Asn Arg Lys Leu Asn Gln Gly Thr Glu
                725                 730                 735
```

-continued

```
Arg His Leu Met His Leu Glu Leu Asp Ile Ser Asp Ser Lys Ile Arg
            740                 745                 750

Tyr Glu Ser Gly Asp His Val Ala Val Tyr Pro Ala Asn Asp Ser Ala
        755                 760                 765

Leu Val Asn Gln Leu Gly Lys Ile Leu Gly Ala Asp Leu Asp Val Val
    770                 775                 780

Met Ser Leu Asn Asn Leu Asp Glu Glu Ser Asn Lys Lys His Pro Phe
785                 790                 795                 800

Pro Cys Pro Thr Ser Tyr Arg Thr Ala Leu Thr Tyr Tyr Leu Asp Ile
                805                 810                 815

Thr Asn Pro Pro Arg Thr Asn Val Leu Tyr Glu Leu Ala Gln Tyr Ala
            820                 825                 830

Ser Glu Pro Ser Glu Gln Glu Leu Leu Arg Lys Met Ala Ser Ser Ser
        835                 840                 845

Gly Glu Gly Lys Glu Leu Tyr Leu Ser Trp Val Val Glu Ala Arg Arg
    850                 855                 860

His Ile Leu Ala Ile Leu Gln Asp Cys Pro Ser Leu Arg Pro Pro Ile
865                 870                 875                 880

Asp His Leu Cys Glu Leu Leu Pro Arg Leu Gln Ala Arg Tyr Tyr Ser
                885                 890                 895

Ile Ala Ser Ser Ser Lys Val His Pro Asn Ser Val His Ile Cys Ala
            900                 905                 910

Val Val Val Glu Tyr Glu Thr Lys Ala Gly Arg Ile Asn Lys Gly Val
        915                 920                 925

Ala Thr Asn Trp Leu Arg Ala Lys Glu Pro Ala Gly Glu Asn Gly Gly
    930                 935                 940

Arg Ala Leu Val Pro Met Phe Val Arg Lys Ser Gln Phe Arg Leu Pro
945                 950                 955                 960

Phe Lys Ala Thr Thr Pro Val Ile Met Val Gly Pro Gly Thr Gly Val
                965                 970                 975

Ala Pro Phe Ile Gly Phe Ile Gln Glu Arg Ala Trp Leu Arg Gln Gln
            980                 985                 990

Gly Lys Glu Val Gly Glu Thr Leu  Leu Tyr Tyr Gly Cys  Arg Arg Ser
        995                 1000                1005

Asp Glu  Asp Tyr Leu Tyr Arg  Glu Glu Leu Ala Gln  Phe His Arg
    1010                1015                1020

Asp Gly  Ala Leu Thr Gln Leu  Asn Val Ala Phe Ser  Arg Glu Gln
    1025                1030                1035

Ser His  Lys Val Tyr Val Gln  His Leu Leu Lys Gln  Asp Arg Glu
    1040                1045                1050

His Leu  Trp Lys Leu Ile Glu  Gly Gly Ala His Ile  Tyr Val Cys
    1055                1060                1065

Gly Asp  Ala Arg Asn Met Ala  Arg Asp Val Gln Asn  Thr Phe Tyr
    1070                1075                1080

Asp Ile  Val Ala Glu Leu Gly  Ala Met Glu His Ala  Gln Ala Val
    1085                1090                1095

Asp Tyr  Ile Lys Lys Leu Met  Thr Lys Gly Arg Tyr  Ser Leu Asp
    1100                1105                1110

Val Trp  Ser Arg Ala Glu Gly  Arg Gly Ser Leu Leu  Thr Cys Gly
    1115                1120                1125

Asp Val  Glu Glu Asn Pro Gly  Pro Met Leu Val Arg  Arg Gly Ala
    1130                1135                1140
```

```
Arg Ala Gly Pro Arg Met Pro Arg Gly Trp Thr Ala Leu Cys Leu
    1145                1150                1155

Leu Ser Leu Leu Pro Ser Gly Phe Met Ser Leu Asp Asn Asn Gly
    1160                1165                1170

Thr Ala Thr Pro Glu Leu Pro Thr Gln Gly Thr Phe Ser Asn Val
    1175                1180                1185

Ser Thr Asn Val Ser Tyr Gln Glu Thr Thr Thr Pro Ser Thr Leu
    1190                1195                1200

Gly Ser Thr Ser Leu His Pro Val Ser Gln His Gly Asn Glu Ala
    1205                1210                1215

Thr Thr Asn Ile Thr Glu Thr Thr Val Lys Phe Thr Ser Thr Ser
    1220                1225                1230

Val Ile Thr Ser Val Tyr Gly Asn Thr Asn Ser Ser Val Gln Ser
    1235                1240                1245

Gln Thr Ser Val Ile Ser Thr Val Phe Thr Thr Pro Ala Asn Val
    1250                1255                1260

Ser Thr Pro Glu Thr Thr Leu Lys Pro Ser Leu Ser Pro Gly Asn
    1265                1270                1275

Val Ser Asp Leu Ser Thr Thr Ser Thr Ser Leu Ala Thr Ser Pro
    1280                1285                1290

Thr Lys Pro Tyr Thr Ser Ser Ser Pro Ile Leu Ser Asp Ile Lys
    1295                1300                1305

Ala Glu Ile Lys Cys Ser Gly Ile Arg Glu Val Lys Leu Thr Gln
    1310                1315                1320

Gly Ile Cys Leu Glu Gln Asn Lys Thr Ser Ser Cys Ala Glu Phe
    1325                1330                1335

Lys Lys Asp Arg Gly Glu Gly Leu Ala Arg Val Leu Cys Gly Glu
    1340                1345                1350

Glu Gln Ala Asp Ala Asp Ala Gly Ala Gln Val Cys Ser Leu Leu
    1355                1360                1365

Leu Ala Gln Ser Glu Val Arg Pro Gln Cys Leu Leu Leu Val Leu
    1370                1375                1380

Ala Asn Arg Thr Glu Ile Ser Ser Lys Leu Gln Leu Met Lys Lys
    1385                1390                1395

His Gln Ser Asp Leu Lys Lys Leu Gly Ile Leu Asp Phe Thr Glu
    1400                1405                1410

Gln Asp Val Ala Ser His Gln Ser Tyr Ser Gln Lys Thr Leu Ile
    1415                1420                1425

Ala Leu Val Thr Ser Gly Ala Leu Leu Ala Val Leu Gly Ile Thr
    1430                1435                1440

Gly Tyr Phe Leu Met Asn Arg Arg Ser Trp Ser Pro Thr Gly Glu
    1445                1450                1455

Arg Leu Glu Leu Glu Pro
    1460


<210> SEQ ID NO 5
<211> LENGTH: 987
<212> TYPE: DNA
<213> ORGANISM: Homo sapiens

<400> SEQUENCE: 5

atgctggtcc gcaggggcgc gcgcgcaggg cccaggatgc cgcggggctg gaccgcgctt     60

tgcttgctga gtttgctgcc ttctgggttc atgagtcttg acaacaacgg tactgctacc    120

ccagagttac ctacccaggg aacattttca aatgtttcta caaatgtatc ctaccaagaa    180
```

```
actacaacac ctagtaccct tggaagtacc agcctgcacc ctgtgtctca acatggcaat    240

gaggccacaa caaacatcac agaaacgaca gtcaaattca catctacctc tgtgataacc    300

tcagtttatg gaaacacaaa ctcttctgtc cagtcacaga cctctgtaat cagcacagtg    360

ttcaccaccc cagccaacgt ttcaactcca gagacaacct tgaagcctag cctgtcacct    420

ggaaatgttt cagacctttc aaccactagc actagccttg caacatctcc cactaaaccc    480

tatacatcat cttctcctat cctaagtgac atcaaggcag aaatcaaatg ttcaggcatc    540

agagaagtga aattgactca gggcatctgc ctggagcaaa ataagacctc cagctgtgcg    600

gagtttaaga aggacagggg agagggcctg gcccgagtgc tgtgtgggga ggagcaggct    660

gatgctgatg ctggggccca ggtatgctcc ctgctccttg cccagtctga ggtgaggcct    720

cagtgtctac tgctggtctt ggccaacaga acagaaattt ccagcaaact ccaacttatg    780

aaaaagcacc aatctgacct gaaaaagctg gggatcctag atttcactga gcaagatgtt    840

gcaagccacc agagctattc ccaaaagacc ctgattgcac tggtcacctc gggagccctg    900

ctggctgtct tgggcatcac tggctatttc ctgatgaatc gccgcagctg gagccccaca    960

ggagaaaggc tggagctgga accctga                                         987


<210> SEQ ID NO 6
<211> LENGTH: 60
<212> TYPE: DNA
<213> ORGANISM: Homo sapiens

<400> SEQUENCE: 6

agagccgagg gcaggggaag tcttctaaca tgcggggacg tggaggaaaa tcccgggccc     60


<210> SEQ ID NO 7
<211> LENGTH: 1047
<212> TYPE: DNA
<213> ORGANISM: Homo sapiens

<400> SEQUENCE: 7

agagccgagg gcaggggaag tcttctaaca tgcggggacg tggaggaaaa tcccgggccc     60

atgctggtcc gcaggggcgc gcgcgcaggg cccaggatgc cgcggggctg gaccgcgctt    120

tgcttgctga gtttgctgcc ttctgggttc atgagtcttg acaacaacgg tactgctacc    180

ccagagttac ctacccaggg aacattttca aatgtttcta caaatgtatc ctaccaagaa    240

actacaacac ctagtaccct tggaagtacc agcctgcacc ctgtgtctca acatggcaat    300

gaggccacaa caaacatcac agaaacgaca gtcaaattca catctacctc tgtgataacc    360

tcagtttatg gaaacacaaa ctcttctgtc cagtcacaga cctctgtaat cagcacagtg    420

ttcaccaccc cagccaacgt ttcaactcca gagacaacct tgaagcctag cctgtcacct    480

ggaaatgttt cagacctttc aaccactagc actagccttg caacatctcc cactaaaccc    540

tatacatcat cttctcctat cctaagtgac atcaaggcag aaatcaaatg ttcaggcatc    600

agagaagtga aattgactca gggcatctgc ctggagcaaa ataagacctc cagctgtgcg    660

gagtttaaga aggacagggg agagggcctg gcccgagtgc tgtgtgggga ggagcaggct    720

gatgctgatg ctggggccca ggtatgctcc ctgctccttg cccagtctga ggtgaggcct    780

cagtgtctac tgctggtctt ggccaacaga acagaaattt ccagcaaact ccaacttatg    840

aaaaagcacc aatctgacct gaaaaagctg gggatcctag atttcactga gcaagatgtt    900

gcaagccacc agagctattc ccaaaagacc ctgattgcac tggtcacctc gggagccctg    960
```

ctggctgtct tgggcatcac tggctatttc ctgatgaatc gccgcagctg gagccccaca 1020
ggagaaaggc tggagctgga accctga 1047

<210> SEQ ID NO 8
<211> LENGTH: 4395
<212> TYPE: DNA
<213> ORGANISM: Homo sapiens

<400> SEQUENCE: 8
atggaactca gcgtcctcct cttccttgca ctcctcacag gactcttgct actcctggtt 60
cagcgccacc ctaacaccca tgaccgcctc ccaccagggc cccgccctct gcccctttttg 120 ggaaaccttc tgcagatgga tagaagaggc ctactcaaat cctttctgag gttccgagag 180
aaatatgggg acgtcttcac ggtacacctg ggaccgaggc ccgtggtcat gctgtgtgga 240
gtagaggcca tacgggaggc ccttgtggac aaggctgagg ccttctctgg ccggggaaaa 300
atcgccatgg tcgacccatt cttccgggga tatggtgtgg tctttgccaa tggaaaccgc 360
tggaaggtgc ttcggcgatt ctctgtgacc actatgaggg acttcgggat gggaaagcgg 420
agtgtggagg agcggattca ggaggaggct cagtgtctga tagaggagct tcggaaatcc 480
aagggggccc tcatggaccc caccttcctc ttccagtcca ttaccgccaa catcatctgc 540
tccatcgtct ttggaaaacg attccactac caagatcaag agttcctgaa gatgatgaac 600
ttgttctacc agactttttc actcatcagc tctgtattcg gccagctgtt tgagctcttc 660
tctggcttct tgaaatactt tcctggggca cacaggcaag tttacaaaaa cctgcaggaa 720
atcaatgctt acattggcca cagtgtggag aagcaccgtg aaaccctgga ccccagcgcc 780
cccaaggacc tcatcgacac ctacctgctc cacatggaaa aagagaaatc caacgcacac 840
agtgaattca gccaccagaa cctcaacctc aacacgctct cgctcttctt tgctggcact 900
gagaccacca gcaccactct ccgctacggc ttcctgctca tgctcaaata ccctcatgtt 960
gcagagagag tctacaggga gattgaacag gtgattggcc cacatcgccc tccagagctt 1020
catgaccgag ccaaaatgcc atacacagag gcagtcatct atgagattca gagattttcc 1080
gaccttctcc ccatgggtgt gccccacatt gtcacccaac acaccagctt ccgagggtac 1140
atcatcccca aggacacaga agtatttctc atcctgagca ctgctctcca tgacccacac 1200
tactttgaaa aaccagacgc cttcaatcct gaccactttc tggatgccaa tggggcactg 1260
aaaaagactg aagcttttat ccccttctcc ttagggaagc ggatttgtct tggtgaaggc 1320
atcgcccgtg cggaattgtt cctcttcttc accaccatcc tccagaactt ctccatggcc 1380
agccccgtgg ccccagaaga catcgatctg acaccccagg agtgtggttg ggcaaaata 1440 cccccaacat accagatccg cttcctgccc cgctcgagct ctacgattca gacattgacc 1500
tcctctgtca gagagagcag ctttgtggaa aagatgaaga aaacggggag gaacatcatc 1560
gtgttctacg gctcccagac ggggactgca gaggagtttg ccaaccgcct gtccaaggac 1620
gcccaccgct acgggatgcg aggcatgtca gcggaccctg aggagtatga cctggccgac 1680
ctgagcagcc tgccagagat cgacaacgcc ctggtggttt tctgcatggc cacctacggt 1740
gagggagacc ccaccgacaa tgcccaggac ttctacgact ggctgcagga gacagacgtg 1800
gatctctctg gggtcaagtt cgcggtgttt ggtcttggga acaagaccta cgagcacttc 1860
aatgccatgg gcaagtacgt ggacaagcgg ctggagcagc tcggcgccca gcgcatcttt 1920
gagctggggt tgggcgacga cgatgggaac ttggaggagg acttcatcac ctggcgagag 1980
cagttctggc cggccgtgtg tgaacacttt ggggtggaag ccactggcga ggagtccagc 2040

```
attcgccagt acgagcttgt ggtccacacc gacatagatg cggccaaggt gtacatgggg   2100
gagatgggcc ggctgaagag ctacgagaac cagaagcccc cctttgatgc caagaatccg   2160
ttcctggctg cagtcaccac caaccggaag ctgaaccagg gaaccgagcg ccacctcatg   2220
cacctggaat tggacatctc ggactccaaa atcaggtatg aatctgggga ccacgtggct   2280
gtgtacccag ccaacgactc tgctctcgtc aaccagctgg gcaaaatcct gggtgccgac   2340
ctggacgtcg tcatgtccct gaacaacctg gatgaggagt ccaacaagaa gcacccattc   2400
ccgtgcccta cgtcctaccg cacggccctc acctactacc tggacatcac caacccgccg   2460
cgtaccaacg tgctgtacga gctggcgcag tacgcctcgg agccctcgga gcaggagctg   2520
ctgcgcaaga tggcctcctc ctccggcgag ggcaaggagc tgtacctgag ctgggtggtg   2580
gaggcccgga ggcacatcct ggccatcctg caggactgcc cgtccctgcg gccccccatc   2640
gaccacctgt gtgagctgct gccgcgcctg caggcccgct actactccat cgcctcatcc   2700
tccaaggtcc accccaactc tgtgcacatc tgtgcggtgg ttgtggagta cgagaccaag   2760
gccggccgca tcaacaaggg cgtggccacc aactggctgc gggccaagga gcctgccggg   2820
gagaacggcg gccgtgcgct ggtgcccatg ttcgtgcgca agtcccagtt ccgcctgccc   2880
ttcaaggcca ccacgcctgt catcatggtg ggccccggca ccggggtggc acccttcata   2940
ggcttcatcc aggagcgggc ctggctgcga cagcagggca aggaggtggg ggagacgctg   3000
ctgtactacg gctgccgccg ctcggatgag gactacctgt accgggagga gctggcgcag   3060
ttccacaggg acggtgcgct cacccagctc aacgtggcct tctcccggga gcagtcccac   3120
aaggtctacg tccagcacct gctaaagcaa gaccgagagc acctgtggaa gttgatcgaa   3180
ggcggtgccc acatctacgt ctgtggggat gcacggaaca tggccaggga tgtgcagaac   3240
accttctacg acatcgtggc tgagctcggg gccatggagc acgcgcaggc ggtggactac   3300
atcaagaaac tgatgaccaa gggccgctac tccctggacg tgtggagcag agccgagggc   3360
aggggaagtc ttctaacatg cggggacgtg gaggaaaatc ccgggcccat gctggtccgc   3420
aggggcgcgc gcgcagggcc caggatgccg cggggctgga ccgcgctttg cttgctgagt   3480
ttgctgcctt ctgggttcat gagtcttgac aacaacggta ctgctacccc agagttacct   3540
acccagggaa cattttcaaa tgtttctaca aatgtatcct accaagaaac tacaacacct   3600
agtacccttg gaagtaccag cctgcaccct gtgtctcaac atggcaatga ggccacaaca   3660
aacatcacag aaacgacagt caaattcaca tctacctctg tgataacctc agtttatgga   3720
aacacaaact cttctgtcca gtcacagacc tctgtaatca gcacagtgtt caccacccca   3780
gccaacgttt caactccaga gacaaccttg aagcctagcc tgtcacctgg aaatgtttca   3840
gacctttcaa ccactagcac tagccttgca acatctccca ctaaacccta tacatcatct   3900
tctcctatcc taagtgacat caaggcagaa atcaaatgtt caggcatcag agaagtgaaa   3960
ttgactcagg gcatctgcct ggagcaaaat aagacctcca gctgtgcgga gtttaagaag   4020
gacaggggag agggcctggc ccgagtgctg tgtggggagg agcaggctga tgctgatgct   4080
ggggcccagg tatgctccct gctccttgcc cagtctgagg tgaggcctca gtgtctactg   4140
ctggtcttgg ccaacagaac agaaatttcc agcaaactcc aacttatgaa aaagcaccaa   4200
tctgacctga aaaagctggg gatcctagat ttcactgagc aagatgttgc aagccaccag   4260
```

-continued

| | |
|---|---|
| agctattccc aaaagaccct gattgcactg gtcacctcgg gagccctgct ggctgtcttg | 4320 |
| ggcatcactg gctatttcct gatgaatcgc cgcagctgga gccccacagg agaaaggctg | 4380 |
| gagctggaac cctga | 4395 |

GENETICALLY MODIFIED HUMAN STEM CELL EXPRESSING A MUTANT HUMAN CYTOCHROME P450 2B6 PROTEIN AND USE THEREOF IN THE TREATMENT OF CANCER

TECHNICAL FIELD

The present invention relates to a genetically modified human stem cell, in which said human stem cell comprises an exogenous nucleic acid comprising a region coding for a fusion protein comprising a mutant human cytochrome P450 2B6 (CYP2B6*) protein of SEQ ID No. 1 or a variant or fragment thereof and an NADPH-cytochrome P450 reductase protein of SEQ ID No. 2 or a variant or fragment thereof, functionally bound to a promoter, said exogenous nucleic acid having been integrated into one of the genomic safe harbors of said human stem cell. The invention also relates to the use of said cell for the treatment of cancer, particularly the solid tumours, and in particular hepatocellular carcinomas.

PRIOR ART

Liver cancers represent over 841,080 new cases worldwide annually, of which 90% are hepatocellular carcinomas. Hepatocellular carcinoma is the third cause of cancer mortality worldwide. Chronic infection by the hepatitis C (VHC) and hepatitis B (VHB) viruses or also alcoholic cirrhosis are the main causes of hepatocellular carcinoma. Furthermore, for the last 10 years, the emergence of nonalcoholic steatohepatitis (NASH) associated with the increase in obesity, pre-diabetic and type-2 diabetes conditions, is an emerging cause of hepatocarcinoma. Treatment for hepatocellular carcinoma is essential in order to avoid a fatal outcome. In light of the increase in patients having non-alcoholic steatohepatitis, it is highly probable that the number of patients with hepatocellular carcinoma will increase in the years to come. The spontaneous survival of patients with hepatocellular carcinoma is no greater than 15 months. The BCLC (Barcelona Cancer Liver Centre) classification allows 5 types of clinical situation to be distinguished.

Stages 0 and A (early stage) (15% of patients) define patients with an early diagnosis of disease, in good general health and having a hepatocellular carcinoma of less than 3 cm. These patients are eligible for tumour resection surgery and liver transplantation, which are the only curative treatments. Survival at 5 years is 60%.

Stage B (intermediate) relates to patients whose general state of health is maintained but having one or more hepatocellular carcinoma(s) the size of which is greater than 3 cm, without invasion of the hepatic portal vein or metastases. These patients may benefit from hepatic chemoembolization with doxorubicin. Median survival for these patients is 20 months.

Stage C (advanced) defines a patient having a hepatocarcinoma with portal invasion, ganglion and pulmonary metastases associated with a moderate change in their general state of health.

The treatment of reference at this advanced stage is Sorafenib, an antiangiogenic multikinase inhibitor administered via oral route, marketed under the name Nexavar® from Onyx/Bayer. In these patients, the median survival is 11 months. Other, second-line treatments have recently been approved. These are Regorafenib (kinase inhibitor) marketed under the name Stivarga® from Bayer and Nivolumab (anti-PD1 antibody) marketed under the name Opdivo®, from BMS. All these treatments have limited efficacy and are responsible for major adverse reactions (diarrhoea, weight loss, hand-foot syndrome and hypophosphataemia, arterial hypertension) often the cause of poor treatment adherence leading to suboptimal results.

Stage D relates to patients who have reached the palliative stage for which only supportive care can be offered.

Thus, a need therefore exists for new efficacious forms of cancer treatment, particularly the solid tumours and in particular hepatocellular carcinomas, in particular treatments capable of supplying controlled and sustained therapy, alone or in combination with other therapies, while improving the quality of life of the patient and reducing the adverse effects associated with the treatment.

In order to prevent and/or treat cancer and/or associated metastases, in particular the solid tumours, and particularly hepatocellular carcinoma and/or associated metastases, the inventors have developed a new genetically modified human stem cell capable of metabolizing cyclophosphamide and inducing immunological death of the tumour cells by eliciting a strong antitumor immune response.

SUMMARY OF THE INVENTION

Thus, the present invention relates to a genetically modified human stem cell, in which said human stem cell comprises an exogenous nucleic acid comprising a region coding for a fusion protein comprising a mutant human cytochrome P450 2B6 (CYP2B6*) protein of SEQ ID No. 1 or a variant or fragment thereof, an NADPH-cytochrome P450 reductase protein of SEQ ID No. 2 or a variant or fragment thereof, functionally bound to a promoter, said exogenous nucleic acid having been integrated into one of the genomic safe harbors of said human stem cell and characterized in that said genetically modified human stem cell is not an embryonic human stem cell.

Advantageously, the human stem cell is chosen from mesenchymal stem cells (hMSC), induced pluripotent stem cells (iPSC) and induced mesenchymal stem cells (iMSC).

Advantageously, the promoter used is a constitutive promoter, preferably the EF1-α promoter. Advantageously, the exogenous nucleic acid further comprises a selectable marker gene.

The present invention also relates to a method for obtaining the genetically modified human stem cell; said human stem cell was obtained by retroviral transduction with a viral vector comprising exogenous nucleic acid.

The present invention also relates to the genetically modified human stem cell for use thereof as a medicament and formulation thereof in a suitable form for administration thereof via transarterial route.

The present invention also relates to a method for selecting genetically modified stem cells comprising the steps of:

a) transducing the human stem cells with a viral vector comprising exogenous nucleic acid,
b) culturing the human stem cells in a predefined culture medium,
c) selecting the genetically modified human stem cells expressing the selectable marker gene on their membrane surface.

The present invention further relates to a pharmaceutical composition comprising the genetically modified human stem cell as active ingredient and at least one pharmaceutically acceptable excipient and optionally at least a second active ingredient, in particular an anti-cancer agent, said pharmaceutical composition being in a form suitable for administration thereof via transarterial route.

The invention also relates to a genetically modified human stem cell or pharmaceutical composition for use thereof in the prevention and/or the treatment of cancer and/or the cancer recurrences and/or associated metastases, preferably of the solid tumours, preferably the hepatocellular carcinomas and/or associated metastases.

DETAILED DESCRIPTION OF THE INVENTION

Thus, the subject of the present invention is a genetically modified human stem cell, in which said human stem cell comprises an exogenous nucleic acid comprising a region coding for a fusion protein comprising a mutant human cytochrome P450 2B6 (CYP2B6*) protein of SEQ ID No. 1 or a variant or fragment thereof, an NADPH-cytochrome P450 reductase protein of SEQ ID No. 2 or a variant or fragment thereof, functionally bound to a promoter, said exogenous nucleic acid having been integrated into one of the safe harbor genes of said human stem cell and characterized in that said genetically modified human stem cell is not an embryonic human stem cell.

The inventors have shown, surprisingly, that the integration of exogenous nucleic acid into one of the genomic safe harbors is of prime importance to enable the genetically modified human stem cell to metabolize cyclophosphamide (CPA) and thus induce immunological death of the tumour cells. In addition, this integration of exogenous nucleic acid into one of the genomic safe harbors allows the genetically modified human stem cell to maintain its morphology and its doubling time. Furthermore, the inventors have shown that a single copy of the exogenous nucleic acid is integrated into one of the genomic safe harbors. The inventors have also shown that the use of genetically modified human stem cells according to the invention allows the complete eradication of solid tumours as well as a protection against recurrences and metastases by vaccinating effect.

In a particular embodiment of the invention, the stem cell is chosen from the human mesenchymal stem cells (hMSC), the induced pluripotent stem cells (iPSC) and the induced mesenchymal stem cells (iMSC).

Within the meaning of the present invention, the term "mesenchymal stem cells" or "hMSC" or "human mesenchymal stem cells" denotes multipotent stem cells capable of differentiating particularly into osteoblasts, chondrocytes, myocytes and adipocytes. The mesenchymal stem cells are located in the mesenchyma, the part of the embryonic mesoderm constituted by loosely packed fusiform or stellate cells. As used here, the mesenchymal stem cells comprise, non-limitatively, CD34-negative stem cells. In an embodiment of the invention, the human mesenchymal stem cells are isolated from the adipose tissue and/or from bone marrow.

Within the meaning of the present invention, the term "induced pluripotent stem cells" or "iPSC" or "human induced pluripotent stem cells" denotes a type of pluripotent stem cell similar to an embryonic stem cell but which is created when somatic cells (for example adult somatic cells) are reprogrammed to enter a state similar to that of an embryonic stem cell while maintaining expression of the factors that are important for maintaining the "pluripotency" of the embryonic stem cells (also called CSE or PSC), i.e. the capability thereof to engage in different differentiation pathways. Such factors can include certain embryonic genes (such as OCT4, SOX2 and LF4 transgenes). As used here, the term "pluripotent" denotes a cell or a cell line capable of differentiating into any differentiated cell type, for example, a capacity to develop into the three germ layers of development of the organism, specifically the endoderm, the mesoderm and the ectoderm.

Within the meaning of the present invention, the term "induced mesenchymal stem cells" or "iMSC" or "human induced mesenchymal stem cells" denotes mesenchymal stem cells derived from induced pluripotent stem cells (iPSC).

In a particular embodiment of the invention, the human stem cell is a mesenchymal stem cell (hMSC). In another particular embodiment of the invention, the human stem cell is an induced pluripotent stem cell (iPSC). In another particular embodiment of the invention, the human stem cell is an induced mesenchymal stem cell (iMSC).

Within the meaning of the present invention, the term "exogenous nucleic acid" denotes a nucleic acid that is not naturally present in the human stem cell according to the invention. The exogenous nucleic acid can be a genomic DNA, cDNA, natural DNA or obtained totally or partially by chemical synthesis. According to an embodiment of the invention, the exogenous nucleic acid has a therapeutic benefit.

In a particularly advantageous embodiment, the exogenous nucleic acid comprises a region coding for a fusion protein comprising a mutant human cytochrome P450 2B6 (CYP2B6*) protein of SEQ ID No. 1 or a variant or fragment thereof, an NADPH-cytochrome P450 reductase protein of SEQ ID No. 2 or a variant or fragment thereof.

In a particularly advantageous embodiment of the invention, the human cytochrome P450 2B6 protein is a mutant human cytochrome P450 2B6 protein, also called CYP2B6*, of SEQ ID No. 1 or a variant or fragment thereof, in which said variant or said fragment comprises 114V, 199M and 477 W residues as represented in the amino acid sequence SEQ ID No. 1.

Advantageously, said variant or fragment preserves a biological activity of a protein having the amino acid sequence SEQ ID No. 1.

```
(CYP2B6*):
                                     SEQ ID No.1
MELSVLLFLALLTGLLLLLVQRHPNTHDRLPPGPRPLPLLGNLLQMDRRG

LLKSFLRFREKYGDVFTVHLGPRPVVMLCGVEAIREALVDKAEAFSGRGK

IAMVDPFFRGYGVVFANGNRWKVLRRFSVTTMRDFGMGKRSVEERIQEEA

QCLIEELRKSKGALMDPTFLFQSITANIICSIVFGKRFHYQDQEFLKMMN

LFYQTFSLISSVFGQLFELFSGFLKYFPGAHRQVYKNLQEINAYIGHSVE

KHRETLDPSAPKDLIDTYLLHMEKEKSNAHSEFSHQNLNLNTLSLFFAGT

ETTSTTLRYGFLLMLKYPHVAERVYREIEQVIGPHRPPELHDRAKMPYTE

AVIYEIQRFSDLLPMGVPHIVTQHTSFRGYIIPKDTEVFLILSTALHDPH

YFEKPDAFNPDHFLDANGALKKTEAFIPFSLGKRICLGEGIARAELFLFF

TTILQNFSMASPVAPEDIDLTPQECGWGKIPPTYQIRFLPR
```

The amino acid sequence of the wild-type (CYP2B6 WT) human cytochrome P450 2B6 protein is represented by the sequence SEQ ID No. 3.

```
(CYP2B6 WT):
                                     SEQ ID No.3
MELSVLLFLALLTGLLLLLVQRHPNTHDRLPPGPRPLPLLGNLLQMDRRG

LLKSFLRFREKYGDVFTVHLGPRPVVMLCGVEAIREALVDKAEAFSGRGK

IAMVDPFFRGYGVIFANGNRWKVLRRFSVTTMRDFGMGKRSVEERIQEEA
```

-continued

QCLIEELRKSKGALMDPTFLFQSITANIICSIVFGKRFHYQDQEFLKMLN

LFYQTFSLISSVFGQLFELFSGFLKYFPGAHRQVYKNLQEINAYIGHSVE

KHRETLDPSAPKDLIDTYLLHMEKEKSNAHSEFSHQNLNLNTLSLFFAGT

ETTSTTLRYGFLLMLKYPHVAERVYREIEQVIGPHRPPELHDRAKMPYTE

AVIYEIQRFSDLLPMGVPHIVTQHTSFRGYIIPKDTEVFLILSTALHDPH

YFEKPDAFNPDHFLDANGALKKTEAFIPFSLGKRICLGEGIARAELFLFF

TTILQNFSMASPVAPEDIDLTPQECGVGKIPPTYQIRFLPR

Advantageously, the mutant human cytochrome P450 2B6 (CYP2B6*) protein has an affinity for CPA that is more than 8 times greater than that of the wild-type protein (CYP2B6 WT), while preserving the same Vmax, particularly owing to the substitutions 1114V, L199M and V477 W as shown in SEQ ID No. 1. As described below, the variants and fragments of the amino acid sequence SEQ ID No. 1 are encompassed within the scope of the invention. However, all the mutant human cytochrome P450 2B6 proteins, variants and fragments of the invention as described herein retain Val in the position corresponding to residue 114 of amino acid sequence SEQ ID No. 1, Met in the position corresponding to residue 199 of amino acid sequence SEQ ID No. 1 and Trp in the position corresponding to residue 477 of the amino acid sequence SEQ ID No. 1.

The amino acid sequence of the wild-type NADPH-cytochrome P450 reductase protein (NADPH WT) is represented by the sequence SEQ ID No. 2. The variants and fragments of the NADPH-cytochrome P450 reductase protein of amino acid sequence SEQ ID No. 2, described below, also fall within the scope of the invention.

(NADPH WT):

SEQ ID No. 2

IQTLTSSVRESSFVEKMKKTGRNIIVFYGSQTGTAEEFANRLSKDAHRYG

MRGMSADPEEYDLADLSSLPEIDNALVVFCMATYGEGDPTDNAQDFYDWL

QETDVDLSGVKFAVFGLGNKTYEHFNAMGKYVDKRLEQLGAQRIFELGLG

DDDGNLEEDFITWREQFWPAVCEHFGVEATGEESSIRQYELVVHTDIDAA

KVYMGEMGRLKSYENQKPPFDAKNPFLAAVTTNRKLNQGTERHLMHLELD

ISDSKIRYESGDHVAVYPANDSALVNQLGKILGADLDVVMSLNNLDEESN

KKHPFPCPTSYRTALTYYLDITNPPRTNVLYELAQYASEPSEQELLRKMA

SSSGEGKELYLSWVVEARRHILAILQDCPSLRPPIDHLCELLPRLQARYY

SIASSSKVHPNSVHICAVVVEYETKAGRINKGVATNWLRAKEPAGENGGR

ALVPMFVRKSQFRLPFKATTPVIMVGPGTGVAPFIGFIQERAWLRQQGKE

VGETLLYYGCRRSDEDYLYREELAQFHRDGALTQLNVAFSREQSHKVYVQ

HLLKQDREHLWKLIEGGAHIYVCGDARNMARDVQNTFYDIVAELGAMEHA

QAVDYIKKLMTKGRYSLDVWS

The variants of the proteins can be natural variants, such as splicing variants, alleles and isoforms, or can be produced by recombinant means. Variations of the amino acid sequence can be introduced by substitution, deletion or insertion of one or more codons in the nucleic acid sequence coding for the protein, leading to a modification of the amino acid sequence of the protein. Optionally, the variation can be of 1, 2, 3, 4, 5, 6, 7, 8, 9, 10, 11, 12, 13, 14, 15, 16, 17, 18, 19, 20 amino acids or more with any other amino acid. In addition or alternatively, the variation can be introduced by addition or deletion of 1, 2, 3, 4, 5, 6, 7, 8, 9, 10, 11, 12, 13, 14, 15, 16, 17, 18, 19, 20 amino acids or more within the protein. The substitutions of amino acids can be conservative or non conservative. Preferably, the substitutions are conservative substitutions, in which an amino acid is substituted for another amino acid having similar structural and/or functional and/or chemical properties. Examples of conservative substitutions are listed below:

Ala (A) Val; Leu; Ile
Arg (R) Lys; Gln; Asn
Asn (N) Gln; His; Lys
Asp (D) Glu
Cys (C) Ser
Gln (Q) Asn
Glu (E) Asp
Gly (G) Pro; Ala; ala
His (H) Asn; Gln; Lys; Arg;
Ile (I) Leu; Val; Met; Ala;
norleucine Leu
Leu (L) norleucine; Ile; Met; Ala; Phe
Lys (K) Arg; Gln; Asn
Met (M) Leu; Phe; Ile
Phe (F) Leu; Val; Ile; Ala; Tyr
Pro (P) Ala
Ser (S) Thr
Thr (T) Ser
Trp (W) Tyr; Phe;
Tyr (Y) Trp; Phe; Thr; Ser;
Val (V) Ile; Leu; Met; Phe; Ala; norleucine.

The protein variants can include proteins that have at least approximately 80% amino acid sequence identity with a polypeptide sequence described herein. Advantageously, a protein variant will have at least approximately 80%, 81%, 82%, 83%, 84%, 85%, 86%, 87%, 88%, 89%, 90%, 91%, 92%, 93%, 94%, 95%, 96%, 97%, 98%, 99% amino acid sequence identity with a complete amino acid sequence or a fragment of an amino acid sequence of SEQ ID No. 1 and/or SEQ ID No. 2.

The amino acid sequence identity is defined as the percentage of amino acid residues of the variant sequence that are identical to the amino acid residues of the sequence of reference, after alignment of the sequences and if necessary, the introduction of holes in order to reach the percentage of maximum sequence identity, not envisaging conservative substitutions within the context of the sequence identity. The sequence identity can be determined over the entire length of the variant sequence, over the entire length of the sequence of reference, or both. The methods of sequent alignment and determination of sequence identity are well known in the art, for example, by using publicly available software such as BioPerl, BLAST, BLAST-2, CS-BLAST, FASTA, ALIGN, ALIGN-2, LALIGN, Jaligner, Matcher or the Megalign software (DNASTAR).

The protein fragments and the protein variants described in the present application are also encompassed by the invention. Such fragments can be truncated at the N-terminal end or at the C-terminal end, or can be devoid of internal amino acid residues outside of the N-terminal and C-terminal ends, for example, with respect to a total-length protein. Certain fragments are devoid of amino acid residues that are not essential to enzyme activity. Advantageously, said fragments are at least approximately 10, 20, 30, 40, 50, 60, 70, 80, 90, 100, 110, 120, 150, 200, 250, 300, 350, 400, 450, 500 amino acids or more in length.

The preferred fragments of the proteins described herein comprise all or part of the active site. The preferred fragments of the mutant human cytochrome P450 2B6 (CYP2B6*) protein comprise or are constituted by amino acids 1 to 490 of the complete-length sequence SEQ ID No. 1. The preferred fragments of NADPH-cytochrome P450 reductase protein comprise or are constituted by fragments comprising or constituted by amino acids 60 to 680 of the amino acid sequence SEQ ID No. 2.

The variants and fragments of the invention preferably preserve a biological activity of the complete protein. The variants and fragments of the human cytochrome P450 2B6 protein advantageously have an oxidation activity of a substrate such as cyclophosphamide (CPA) or another substrate, in particular by catalysing 4-OH-CPA hydroxylation.

In a particularly advantageous embodiment, said variants and fragments have an affinity for cyclophosphamide (CPA) greater than that of the human cytochrome P450 2B6 protein of sequence SEQ ID No. 3, preferably at least 2, 3, 4, 5, 6, 7, 8, 9 or 10 times that of the wild-type sequence.

In a particularly advantageous embodiment, said variants and fragments have an affinity for CPA that is identical, substantially identical or greater than that of the mutant human cytochrome P450 2B6 protein (CYP2B6*) of SEQ ID No. 1. Methods making it possible to assay said activity and said affinity are well known to a person skilled in the art and are particularly described in Nguyen et al., Mol. Pharmacol., 2008, 73: 1,122-1,133.

The variants and the fragments of the NADPH-cytochrome P450 reductase protein preferably have an activity of reduction of cytochrome c, preferably NADPH-dependent.

In a preferred embodiment, said variants and fragments have an activity that is identical, substantially greater than or equal to that of the complete-length NADPH-cytochrome P450 reductase protein (SEQ ID No. 2). Methods for assaying said activity are well known to a person skilled in the art and are particularly described in Yasukochi et al; Arch. Biochem. Biophys, 1980, 202: 491-498.

A person skilled in the art will be able to determine the amino acid residues that can be inserted, substituted or deleted without detracting from the activity of the protein, using knowledge of the protein structure available in the art and the publicly available molecular modelling techniques (see for example Nguyen et al. Mol. Pharmacol. 2008, 73: 1,122-1,133). The authorized variation can be determined by systematically carrying out amino acid insertions, deletions or substitutions in the sequence and testing the resulting variants for the activity demonstrated with respect to the wild protein.

Within the meaning of the present invention, the term "fusion protein" denotes a chimeric protein created by joining two or more genes coding for distinct proteins or protein fragments, such as different proteinaceous domains, in a single reading frame coding for a single translated protein.

The fusion protein of the present invention preferably comprises:

- a mutant human cytochrome P450 2B6 (CYP2B6*) protein of SEQ ID No. 1 or a variant or fragment thereof, and
- an NADPH-cytochrome P450 reductase protein of SEQ ID No. 2 or a variant or fragment thereof as described above.

In a particularly advantageous embodiment, said fusion protein of sequence SEQ ID No. 4 comprises:

- residues 1 to 490 of the mutant human cytochrome P450 2B6 (CYP2B6*) protein of SEQ ID No. 1 or a variant or fragment thereof and
- residues 57 to 678 of the NADPH-cytochrome P450 reductase protein of SEQ ID No. 2 or a variant or fragment thereof.

```
(fusion protein):
                                                SEQ ID No.4
MELSVLLFLALLTGLLLLLVQRHPNTHDRLPPGPRPLPLLGNLLQMDRRG

LLKSFLRFREKYGDVFTVHLGPRPVVMLCGVEAIREALVDKAEAFSGRGK

IAMVDPFFRGYGVVFANGNRWKVLRRFSVTTMRDFGMGKRSVEERIQEEA

QCLIEELRKSKGALMDPTFLFQSITANIICSIVFGKRFHYQDQEFLKMMN

LFYQTFSLISSVFGQLFELFSGFLKYFPGAHRQVYKNLQEINAYIGHSVE

KHRETLDPSAPKDLIDTYLLHMEKEKSNAHSEFSHQNLNLNTLSLFFAGT

ETTSTTLRYGFLLMLKYPHVAERVYREIEQVIGPHRPPELHDRAKMPYTE

AVIYEIQRFSDLLPMGVPHIVTQHTSFRGYIIPKDTEVFLILSTALHDPH

YFEKPDAFNPDHFLDANGALKKTEAFIPFSLGKRICLGEGIARAELFLFF

TTILQNFSMASPVAPEDIDLTPQECGWGKIPPTYQIRFLPRSSSTIQTLT

SSVRESSFVEKMKKTGRNIIVFYGSQTGTAEEFANRLSKDAHRYGMRGMS

ADPEEYDLADLSSLPEIDNALVVFCMATYGEGDPTDNAQDFYDWLQETDV

DLSGVKFAVFGLGNKTYEHFNAMGKYVDKRLEQLGAQRIFELGLGDDDGN

LEEDFITWREQFWPAVCEHFGVEATGEESSIRQYELVVHTDIDAAKVYMG

EMGRLKSYENQKPPFDAKNPFLAAVTTNRKLNQGTERHLMHLELDISDSK

IRYESGDHVAVYPANDSALVNQLGKILGADLDVVMSLNNLDEESNKKHPF

PCPTSYRTALTYYLDITNPPRTNVLYELAQYASEPSEQELLRKMASSSGE

GKELYLSWVVEARRHILAILQDCPSLRPPIDHLCELLPRLQARYYSIASS

SKVHPNSVHICAVVVEYETKAGRINKGVATNWLRAKEPAGENGGRALVPM

FVRKSQFRLPFKATTPVIMVGPGTGVAPFIGFIQERAWLRQQGKEVGETL

LYYGCRRSDEDYLYREELAQFHRDGALTQLNVAFSREQSHKVYVQHLLKQ

DREHLWKLIEGGAHIYVCGDARNMARDVQNTFYDIVAELGAMEHAQAVDY

IKKLMTKGRYSLDVWSRAEGRGSLLTCGDVEENPGPMLVRRGARAGPRMP

RGWTALCLLSLLPSGFMSLDNNGTATPELPTQGTFSNVSTNVSYQETTTP

STLGSTSLHPVSQHGNEATTNITETTVKFTSTSVITSVYGNTNSSVQSQT

SVISTVFTTPANVSTPETTLKPSLSPGNVSDLSTTSTSLATSPTKPYTSS

SPILSDIKAEIKCSGIREVKLTQGICLEQNKTSSCAEFKKDRGEGLARVL

CGEEQADADAGAQVCSLLLAQSEVRPQCLLLVLANRTEISSKLQLMKKHQ

SDLKKLGILDFTEQDVASHQSYSQKTLIALVTSGALLAVLGITGYFLMNR

RSWSPTGERLELEP*.
```

The mutant human cytochrome P450 2B6 (CYP2B6*) protein of SEQ ID No. 1 or a variant or fragment thereof can be upstream or downstream of the NADPH-cytochrome P450 reductase protein of SEQ ID No. 2 or a variant or fragment thereof. Preferably, the mutant human cytochrome P450 2B6 (CYP2B6*) protein of SEQ ID No. 1 or a variant or fragment thereof is upstream of the NADPH-cytochrome P450 reductase protein of SEQ ID No. 2 or a variant or fragment thereof.

When the context permits, the term "proteins of the invention" and "the proteins disclosed herein" must be understood as encompassing said fusion proteins.

The proteins or protein fragments constituting the fusion protein can be separated by a linking peptide sequence or a spacer. The linking peptide sequence, also called "linker", or spacer, serves to separate the proteins or the protein fragments of which they are composed, and assist the folding and the efficacious activity of the individual components. The linker or spacer peptide sequence can comprise an enzyme cleavage site to allow the polypeptide components to be separated by enzyme digestion. The linker or spacer peptide sequence can be, for example, of 1, 2, 3, 4, 5, 6, 7, 8, 9, 10, 11, 12, 13, 14, 15 amino acids or more. Preferably, the linker or spacer peptide sequence has a length less than 10, less than 9, less than 8, less than 7, less than 6 or less than 5 amino acids. Examples of linker or spacer peptide sequence to be used in the fusion proteins of the present invention comprise $(Ser)_n$Thr, where "n" is an integer, preferably 1, 2, 3, 4, 5, 6, 7, 8 or 9. In a preferred embodiment, the value of "n" is 5. In another preferred embodiment, the value of "n" is 3.

Within the meaning of the present invention, the term "genomic safe harbor" or "safe harbor" denotes a region of the genome where it is possible to integrate genetic material without disturbing the function, transcription and regulation of the native coding sequences, as well as the genetic structure. A "safe harbor" allows sufficient expression of the exogenous nucleic acid without predisposing the human stem cell according to the invention to a malignant transformation or affecting the function thereof.

In a particular embodiment of the invention, the exogenous nucleic acid is integrated into one of the genomic safe harbors. Advantageously, the exogenous nucleic acid is integrated into one of the genomic safe harbors selected from: the AAVS1 site on chromosome 19, the CCR5 site on chromosome 3, the hROSA26 site on chromosome 3, the 323 site on chromosome 1, the 325 site on chromosome 8, the 289 site on chromosome 1, the 227 site on chromosome 1, the 229 site on chromosome 2, the 253 site on chromosome 2, the 255 site on chromosome 5, the 257 site on chromosome 7, the 259 site on chromosome 14, the 261 site on chromosome 17, the 263 site on chromosome X, the 317 site on chromosome 2, the 303 site on chromosome 2, the 331 site on chromosome 3, the 283 site on chromosome 4, the 231 site on chromosome 4, the 315 site on chromosome 5, the 327 site on chromosome 5, the 305 site on chromosome 5, the 307 site on chromosome 16, the 309 site on chromosome 20, the 285 site on chromosome 6, the 233 site on chromosome 6, the 311 site on chromosome 6, the 299 site on chromosome 6, the 301 site on chromosome 7, the 293 site on chromosome 8, the 319 site on chromosome 11, the 333 site on chromosome 12, the 295 site on chromosome 12, the 329 site on chromosome 12, the 297 site on chromosome 17, the 291 site on chromosome 22, the 313 site on chromosome X and the 321 site on chromosome X.

In a particular embodiment of the invention, the promoter to which the region coding for a fusion protein is functionally linked, comprising a mutant human cytochrome P450 2B6 (CYP2B6*) protein of SEQ ID No. 1 or a variant or fragment thereof, an NADPH-cytochrome P450 reductase protein of SEQ ID No. 2 or a variant or fragment thereof, is a constitutive promoter. Advantageously, the constitutive promoter can be selected from the CMV promoter, the CBA promoter and the EF1-α promoter. Advantageously, the constitutive promoter is the EF1-α promoter.

In a particular embodiment of the invention, the exogenous nucleic acid also comprises a selectable marker gene. By "selectable marker gene" is meant within the meaning of the present invention, a sequence coding for a selectable marker protein, which allows the selective retention of the human stem cells having integrated the exogenous nucleic acid during the culture and propagation of the cells. Advantageously, the selectable marker gene is the CD34 gene; advantageously the CD34 gene having undergone splicing, also called spliced CD34 gene.

Advantageously, the selectable marker gene is the spliced CD34 gene of sequence SEQ ID No. 5:

```
(Spliced CD34 selectable marker qene):
                                          SEQ ID No. 5
ATGCTGGTCCGCAGGGGCGCGCGCAGGGCCCAGGATGCCGCGGGGCTG

GACCGCGCTTTGCTTGCTGAGTTTGCTGCCTTCTGGGTTCATGAGTCTTG

ACAACAACGGTACTGCTACCCCAGAGTTACCTACCCAGGGAACATTTTCA

AATGTTTCTACAAATGTATCCTACCAAGAAACTACAACACCTAGTACCCT

TGGAAGTACCAGCCTGCACCCTGTGTCTCAACATGGCAATGAGGCCACAA

CAAACATCACAGAAACGACAGTCAAATTCACATCTACCTCTGTGATAACC

TCAGTTTATGGAAACACAAACTCTTCTGTCCAGTCACAGACCTCTGTAAT

CAGCACAGTGTTCACCACCCCAGCCAACGTTTCAACTCCAGAGACAACCT

TGAAGCCTAGCCTGTCACCTGGAAATGTTTCAGACCTTTCAACCACTAGC

ACTAGCCTTGCAACATCTCCCACTAAACCCTATACATCATCTTCTCCTAT

CCTAAGTGACATCAAGGCAGAAATCAAATGTTCAGGCATCAGAGAAGTGA

AATTGACTCAGGGCATCTGCCTGGAGCAAAATAAGACCTCCAGCTGTGCG

GAGTTTAAGAAGGACAGGGGAGAGGGCCTGGCCCGAGTGCTGTGTGGGGA

GGAGCAGGCTGATGCTGATGCTGGGGCCCAGGTATGCTCCCTGCTCCTTG

CCCAGTCTGAGGTGAGGCCTCAGTGTCTACTGCTGGTCTTGGCCAACAGA

ACAGAAATTTCCAGCAAACTCCAACTTATGAAAAAGCACCAATCTGACCT

GAAAAAGCTGGGGATCCTAGATTTCACTGAGCAAGATGTTGCAAGCCACC

AGAGCTATTCCCAAAAGACCCTGATTGCACTGGTCACCTCGGGAGCCCTG

CTGGCTGTCTTGGGCATCACTGGCTATTTCCTGATGAATCGCCGCAGCTG

GAGCCCCACAGGAGAAAGGCTGGAGCTGGAACCCTGA
```

The use of the spliced CD34 gene makes it possible to select the human stem cells having integrated the exogenous nucleic acid without having signal transduction activity. In a particularly advantageous embodiment, the spliced CD34 selectable marker gene is functionally linked to a nucleic acid of sequence SEQ ID No. 6 coding for the 2A peptide.

```
(2A peptide):
                                          SEQ ID No. 6
AGAGCCGAGGGCAGGGGAAGTCTTCTAACATGCGGGGACGTGGAGGAAAA

TCCCGGGCCC
```

The spliced CD34 selectable marker gene is functionally linked to a nucleic acid coding for the 2A peptide and is represented by the nucleic acid sequence SEQ ID No. 7.

```
(Spliced CD34 selectable marker gene -
2A peptide):
                                          SEQ ID No. 7
AGAGCCGAGGGCAGGGGAAGTCTTCTAACATGCGGGGACGTGGAGGAAAA

TCCCGGGCCCATGCTGGTCCGCAGGGGCGCGCGCAGGGCCCAGGATGC
```

-continued

CGCGGGGCTGGACCGCGCTTTGCTTGCTGAGTTTGCTGCCTTCTGGGTTC

ATGAGTCTTGACAACAACGGTACTGCTACCCCAGAGTTACCTACCCAGGG

AACATTTTCAAATGTTTCTACAAATGTATCCTACCAAGAAACTACAACAC

CTAGTACCCTTGGAAGTACCAGCCTGCACCCTGTGTCTCAACATGGCAAT

GAGGCCACAACAAACATCACAGAAACGACAGTCAAATTCACATCTACCTC

TGTGATAACCTCAGTTTATGGAAACACAAACTCTTCTGTCCAGTCACAGA

CCTCTGTAATCAGCACAGTGTTCACCACCCCAGCCAACGTTTCAACTCCA

GAGACAACCTTGAAGCCTAGCCTGTCACCTGGAAATGTTTCAGACCTTTC

AACCACTAGCACTAGCCTTGCAACATCTCCCACTAAACCCTATACATCAT

CTTCTCCTATCCTAAGTGACATCAAGGCAGAAATCAAATGTTCAGGCATC

AGAGAAGTGAAATTGACTCAGGGCATCTGCCTGGAGCAAAATAAGACCTC

CAGCTGTGCGGAGTTTAAGAAGGACAGGGGAGAGGGCCTGGCCCGAGTGC

TGTGTGGGGAGGAGCAGGCTGATGCTGATGCTGGGGCCCAGGTATGCTCC

CTGCTCCTTGCCCAGTCTGAGGTGAGGCCTCAGTGTCTACTGCTGGTCTT

GGCCAACAGAACAGAAATTTCCAGCAAACTCCAACTTATGAAAAAGCACC

AATCTGACCTGAAAAAGCTGGGGATCCTAGATTTCACTGAGCAAGATGTT

GCAAGCCACCAGAGCTATTCCCAAAAGACCCTGATTGCACTGGTCACCTC

GGGAGCCCTGCTGGCTGTCTTGGGCATCACTGGCTATTTCCTGATGAATC

GCCGCAGCTGGAGCCCCACAGGAGAAAGGCTGGAGCTGGAACCCTGA

Another subject of the invention relates to an expression vector, for example a viral vector, comprising the exogenous nucleic acid as defined above.

Within the meaning of the present invention, the term "vector" denotes a polynucleotide sequence containing the exogenous nucleic acid as defined above and functionally linked control sequences, so that the transformed human stem cells with these sequences are capable of producing encoded proteins, in particular the fusion protein comprising a mutant human cytochrome P450 2B6 (CYP2B6*) protein of SEQ ID No. 1 or a variant or fragment thereof and an NADPH-cytochrome P450 reductase protein of SEQ ID No. 2 or a variant or fragment thereof.

In a particular embodiment, the human stem cell was obtained by retroviral transduction with a viral vector comprising the exogenous nucleic acid.

The vector generally contains a promoter, initiation and termination signals of the translation, as well as suitable transcription regulation regions. In a particularly advantageous embodiment of the invention, the vector comprises a nucleic acid of sequence SEQ ID No. 8 comprising:

- the exogenous nucleic acid comprising a region coding for a fusion protein comprising a mutant human cytochrome P450 2B6 (CYP2B6*) protein of SEQ ID No. 1 or a variant or fragment thereof and an NADPH-cytochrome P450 reductase protein of SEQ ID No. 2 or a variant or fragment thereof as defined above, and
- the selectable marker gene functionally linked to a nucleic acid coding for the 2A peptide as defined above.

(vectorized nucleic acid):

SEQ ID No. 8

ATGGAACTCAGCGTCCTCCTCTTCCTTGCACTCCTCACAGGACTCTTGCT

ACTCCTGGTTCAGCGCCACCCTAACACCCATGACCGCCTCCCACCAGGGC

CCCGCCCTCTGCCCCTTTTGGGAAACCTTCTGCAGATGGATAGAAGAGGC

CTACTCAAATCCTTTCTGAGGTTCCGAGAGAAATATGGGGACGTCTTCAC

GGTACACCTGGGACCGAGGCCCGTGGTCATGCTGTGTGGAGTAGAGGCCA

TACGGGAGGCCCTTGTGGACAAGGCTGAGGCCTTCTCTGGCCGGGGAAAA

ATCGCCATGGTCGACCCATTCTTCCGGGGATATGGTGTGGTCTTTGCCAA

TGGAAACCGCTGGAAGGTGCTTCGGCGATTCTCTGTGACCACTATGAGGG

ACTTCGGGATGGGAAAGCGGAGTGTGGAGGAGCGGATTCAGGAGGAGGCT

CAGTGTCTGATAGAGGAGCTTCGGAAATCCAAGGGGGCCCTCATGGACCC

CACCTTCCTCTTCCAGTCCATTACCGCCAACATCATCTGCTCCATCGTCT

TTGGAAAACGATTCCACTACCAAGATCAAGAGTTCCTGAAGATGATGAAC

TTGTTCTACCAGACTTTTTCACTCATCAGCTCTGTATTCGGCCAGCTGTT

TGAGCTCTTCTCTGGCTTCTTGAAATACTTTCCTGGGGCACACAGGCAAG

TTTACAAAAACCTGCAGGAAATCAATGCTTACATTGGCCACAGTGTGGAG

AAGCACCGTGAAACCCTGGACCCCAGCGCCCCCAAGGACCTCATCGACAC

CTACCTGCTCCACATGGAAAAAGAGAAATCCAACGCACACAGTGAATTCA

GCCACCAGAACCTCAACCTCAACACGCTCTCGCTCTTCTTTGCTGGCACT

GAGACCACCAGCACCACTCTCCGCTACGGCTTCCTGCTCATGCTCAAATA

CCCTCATGTTGCAGAGAGAGTCTACAGGGAGATTGAACAGGTGATTGGCC

CACATCGCCCTCCAGAGCTTCATGACCGAGCCAAAATGCCATACACAGAG

GCAGTCATCTATGAGATTCAGAGATTTTCCGACCTTCTCCCCATGGGTGT

GCCCCACATTGTCACCCAACACACCAGCTTCCGAGGGTACATCATCCCCA

AGGACACAGAAGTATTTCTCATCCTGAGCACTGCTCTCCATGACCCACAC

TACTTTGAAAAACCAGACGCCTTCAATCCTGACCACTTTCTGGATGCCAA

TGGGGCACTGAAAAAGACTGAAGCTTTTATCCCCTTCTCCTTAGGGAAGC

GGATTTGTCTTGGTGAAGGCATCGCCCGTGCGGAATTGTTCCTCTTCTTC

ACCACCATCCTCCAGAACTTCTCCATGGCCAGCCCCGTGGCCCCAGAAGA

CATCGATCTGACACCCCAGGAGTGTGGTTGGGGCAAAATACCCCCAACAT

ACCAGATCCGCTTCCTGCCCCGCTCGAGCTCTACGATTCAGACATTGACC

TCCTCTGTCAGAGAGAGCAGCTTTGTGGAAAAGATGAAGAAAACGGGGAG

GAACATCATCGTGTTCTACGGCTCCCAGACGGGGACTGCAGAGGAGTTTG

CCAACCGCCTGTCCAAGGACGCCCACCGCTACGGGATGCGAGGCATGTCA

GCGGACCCTGAGGAGTATGACCTGGCCGACCTGAGCAGCCTGCCAGAGAT

CGACAACGCCCTGGTGGTTTTCTGCATGGCCACCTACGGTGAGGGAGACC

CCACCGACAATGCCCAGGACTTCTACGACTGGCTGCAGGAGACAGACGTG

GATCTCTCTGGGGTCAAGTTCGCGGTGTTTGGTCTTGGGAACAAGACCTA

CGAGCACTTCAATGCCATGGGCAAGTACGTGGACAAGCGGCTGGAGCAGC

TCGGCGCCCAGCGCATCTTTGAGCTGGGGTTGGGCGACGACGATGGGAAC

TTGGAGGAGGACTTCATCACCTGGCGAGAGCAGTTCTGGCCGGCCGTGTG

TGAACACTTTGGGGTGGAAGCCACTGGCGAGGAGTCCAGCATTCGCCAGT

ACGAGCTTGTGGTCCACACCGACATAGATGCGGCCAAGGTGTACATGGGG

-continued

```
GAGATGGGCCGGCTGAAGAGCTACGAGAACCAGAAGCCCCCCTTTGATGC
CAAGAATCCGTTCCTGGCTGCAGTCACCACCAACCGGAAGCTGAACCAGG
GAACCGAGCGCCACCTCATGCACCTGGAATTGGACATCTCGGACTCCAAA
ATCAGGTATGAATCTGGGGACCACGTGGCTGTGTACCCAGCCAACGACTC
TGCTCTCGTCAACCAGCTGGGCAAAATCCTGGGTGCCGACCTGGACGTCG
TCATGTCCCTGAACAACCTGGATGAGGAGTCCAACAAGAAGCACCCATTC
CCGTGCCCTACGTCCTACCGCACGGCCCTCACCTACTACCTGGACATCAC
CAACCCGCCGCGTACCAACGTGCTGTACGAGCTGGCGCAGTACGCCTCGG
AGCCCTCGGAGCAGGAGCTGCTGCGCAAGATGGCCTCCTCCTCCGGCGAG
GGCAAGGAGCTGTACCTGAGCTGGGTGGTGGAGGCCCGGAGGCACATCCT
GGCCATCCTGCAGGACTGCCCGTCCCTGCGGCCCCCCATCGACCACCTGT
GTGAGCTGCTGCCGCGCCTGCAGGCCCGCTACTACTCCATCGCCTCATCC
TCCAAGGTCCACCCCAACTCTGTGCACATCTGTGCGGTGGTTGTGGAGTA
CGAGACCAAGGCCGGCCGCATCAACAAGGGCGTGGCCACCAACTGGCTGC
GGGCCAAGGAGCCTGCCGGGGAGAACGGCGGCCGTGCGCTGGTGCCCATG
TTCGTGCGCAAGTCCCAGTTCCGCCTGCCCTTCAAGGCCACCACGCCTGT
CATCATGGTGGGCCCCGGCACCGGGGTGGCACCCTTCATAGGCTTCATCC
AGGAGCGGGCCTGGCTGCGACAGCAGGGCAAGGAGGTGGGGGAGACGCTG
CTGTACTACGGCTGCCGCCGCTCGGATGAGGACTACCTGTACCGGGAGGA
GCTGGCGCAGTTCCACAGGGACGGTGCGCTCACCCAGCTCAACGTGGCCT
TCTCCCGGGAGCAGTCCCACAAGGTCTACGTCCAGCACCTGCTAAAGCAA
GACCGAGAGCACCTGTGGAAGTTGATCGAAGGCGGTGCCCACATCTACGT
CTGTGGGGATGCACGGAACATGGCCAGGGATGTGCAGAACACCTTCTACG
ACATCGTGGCTGAGCTCGGGGCCATGGAGCACGCGCAGGCGGTGGACTAC
ATCAAGAAACTGATGACCAAGGGCCGCTACTCCCTGGACGTGTGGAGCAG
AGCCGAGGGCAGGGGAAGTCTTCTAACATGCGGGGACGTGGAGGAAAATC
CCGGGCCCATGCTGGTCCGCAGGGGCGCGCGCGCAGGGCCCAGGATGCCG
CGGGGCTGGACCGCGCTTTGCTTGCTGAGTTTGCTGCCTTCTGGGTTCAT
GAGTCTTGACAACAACGGTACTGCTACCCCAGAGTTACCTACCCAGGGAA
CATTTTCAAATGTTTCTACAAATGTATCCTACCAAGAAACTACAACACCT
AGTACCCTTGGAAGTACCAGCCTGCACCCTGTGTCTCAACATGGCAATGA
GGCCACAACAAACATCACAGAAACGACAGTCAAATTCACATCTACCTCTG
TGATAACCTCAGTTTATGGAAACACAAACTCTTCTGTCCAGTCACAGACC
TCTGTAATCAGCACAGTGTTCACCACCCCAGCCAACGTTTCAACTCCAGA
GACAACCTTGAAGCCTAGCCTGTCACCTGGAAATGTTTCAGACCTTTCAA
CCACTAGCACTAGCCTTGCAACATCTCCCACTAAACCCTATACATCATCT
TCTCCTATCCTAAGTGACATCAAGGCAGAAATCAAATGTTCAGGCATCAG
AGAAGTGAAATTGACTCAGGGCATCTGCCTGGAGCAAAATAAGACCTCCA
GCTGTGCGGAGTTTAAGAAGGACAGGGGAGAGGGCCTGGCCCGAGTGCTG
TGTGGGGAGGAGCAGGCTGATGCTGATGCTGGGGCCCAGGTATGCTCCCT
GCTCCTTGCCCAGTCTGAGGTGAGGCCTCAGTGTCTACTGCTGGTCTTGG
```

-continued

```
CCAACAGAACAGAAATTTCCAGCAAACTCCAACTTATGAAAAAGCACCAA
TCTGACCTGAAAAAGCTGGGGATCCTAGATTTCACTGAGCAAGATGTTGC
AAGCCACCAGAGCTATTCCCAAAAGACCCTGATTGCACTGGTCACCTCGG
GAGCCCTGCTGGCTGTCTTGGGCATCACTGGCTATTTCCTGATGAATCGC
CGCAGCTGGAGCCCCACAGGAGAAAGGCTGGAGCTGGAACCCTGA
```

In a particular embodiment of the invention, the vector used is a lentiviral vector, advantageously the lentiviral vector pLenti-III-EF1α, marketed by the company Applied Biological Materials Inc.

The vector is held stable in the human stem cell and can optionally possess particular signals that specify the secretion of the translated protein. These different elements are selected and optimized by a person skilled in the art as a function of the host cell used. Such vectors are prepared by methods habitually used by a person skilled in the art, and the resulting clones can be introduced into the appropriate human stem cell by standard methods, such as lipofection, electroporation, the use of polycationic agents, thermal shock, or chemical methods.

In another particular embodiment of the invention, the exogenous nucleic acid can be introduced by different methods into one of the one of the genomic safe harbors, particularly by using effector nucleation techniques of the transcription activator-like effector nuclease (TALEN) type, grouped together as clustered regularly interspaced short palindromic repeats (CRISPR/Cas9) or zinc finger nuclease (ZFN) techniques. Advantageously, the integration of the exogenous nucleic acid in one of the genomic safe harbors is obtained by using clustered regularly interspaced short palindromic repeats (CRISPR/Cas9). Use of this technology in genome editing is well described in the art. In summary, CRISPR is a microbial nuclease system involved in defence against invasive phages and plasmids. The CRISPR loci in microbial hosts contain a combination of genes (Cas) associated with CRISPR as well as non-coding RNA elements capable of programming the cleavage specificity of the nucleic acids (sgRNA) induced by CRISPR. Three types (I-III) of CRISPR systems have been identified over a wide range of bacterial hosts. A key characteristic of each CRISPR locus is the presence of a table of repetitive sequences (direct repetitions) interspersed with short sequences of non-repetitive sequences (spacers). The non-coding CRISPR array is transcribed and cleaved within short direct rcRNA repetitions containing individual spacer sequences, which direct the Cas nucleases to the target site (protospacer). The type II CRISPR is one of the systems that are the best characterized, and produces a targeted double strand DNA break in four sequential steps. Firstly, two noncoding RNAs, the pre-rRNA array and the tracrRNA, are transcribed from the CRISPR locus. Secondly, the tracrRNA hybridizes to the repeat regions of the pre-tRNA and intervenes in processing pre-rRNA into mature rRNA containing individual spacer sequences. Thirdly, the mature tRNA: tracrRNA complex directs Cas9 to the target DNA via matching of the Watson-Crick bases between the spacer situated on the rRNA and the protospacer situated on the target DNA, beside the protospacer adjacent motif (PAM), a supplementary requirement for recognition of the target. Finally, Cas9 intervenes in the cleavage of the target DNA in order to create a double-strand break in the protospacer. Cas9 is therefore the characteristic protein of the CRISPR-Cas type II system and a big monomer DNA nuclease guided towards a target DNA sequence adjacent to the PAM (protospacer adjacent motif) sequence by a complex of two noncoding RNAs: CRISPR RNA (rRNA) and trans-activating rRNA (tracrRNA). The Cas9 protein contains two nuclease domains homologous to the RuvC and HNH nucleases. The HNH nuclease domain cleaves the complementary DNA strand while the RuvC domain cleaves the non-complementary strand and, consequently, a complete cut is introduced in the target DNA. The heterologous expression of Cas9 with an sgRNA can introduce specific double-strand breaks (DSB) at the site in the genomic DNA of living cells of various organisms. For applications in eucaryotic organisms, Cas9 codon-optimized versions, originating from the bacterium *Streptococcus pyogenes*, were used. Single guide RNA (sgRNA) is the second component of the CRISPR/Cas system that forms a complex with the Cas9 nuclease. The sgRNA is a synthetic RNA chimera created by the fusion of cRNA and tracrRNA. The gRNA guide sequence situated at the 5' end confers the specificity on the target DNA. Consequently, by modifying the guide sequence, it is possible to create sgRNAs with different target specificities. The canonical length of the guide sequence is 20 bp. The Cas9 expression vectors intended to be used in the methods of the invention can be constructed as described in the art.

Another subject of the invention relates to the genetically modified human stem cell as defined above for use thereof as a medicament. In particular, the present invention relates to the genetically modified human stem cell as defined above for use thereof in the prevention and/or the treatment of cancer and/or cancer recurrences and/or associated metastases.

Advantageously, the cancer is a cancer selected from: cancers affecting the central nervous system, such as astrocytomas and gliomas; cancers of the upper aerodigestive tract (ENT), such as cancer of the lips, cancer of the oral cavity, oropharyngeal and nasopharyngeal cancer; cancers of the endocrine glands, such as thyroid cancer, cancer of the adrenal glands and extra-digestive and pulmonary neuroendocrine tumours; cancers of the exocrine glands, such as breast cancer and pancreatic cancer; cancers affecting the thorax, such as pleural and lung cancer; digestive system cancers, such as cancer of the oesophagus, stomach cancer, small bowel cancer, colon cancer and rectal and/or anal cancer; genital cancers, such as prostate cancer, cervical cancer, endometrial cancer, cancer of the vagina and cancer of the vulva; urinary system cancers, such as kidney cancer and bladder cancer; sarcomas, such as soft tissue sarcoma, gastro-intestinal stromal tumours (GIST) and bone sarcoma; skin cancers, such as melanoma; hepatobiliary cancers, such as hepatocellular carcinoma and cholangiocarcinoma, the list being non-limitative.

Advantageously, the invention relates to the genetically modified human stem cell as defined above for use thereof in the prevention and/or the treatment of the solid tumours, in particular hepatocellular carcinomas, and/or cancer recurrences and/or associated metastases.

According to a particularly advantageous embodiment of the invention, the genetically modified human stem cell according to the invention is particularly useful for preventing and/or treating cancer and/or cancer recurrences and/or associated metastases.

According to a particularly advantageous embodiment of the invention, the genetically modified human stem cell according to the invention is particularly useful for preventing and/or treating the solid tumours and/or cancer recurrences and/or associated metastases.

According to a particularly advantageous embodiment of the invention, the genetically modified human stem cell according to the invention is particularly useful for preventing and/or treating a cancer and/or cancer recurrences and/or associated metastases selected from: cancers affecting the central nervous system, such as astrocytomas and gliomas; cancers of the upper aerodigestive tract (ENT), such as cancer of the lips, cancer of the oral cavity, oropharyngeal and nasopharyngeal cancer; cancers of the endocrine glands, such as thyroid cancer, cancer of the adrenal glands and extra-digestive and pulmonary neuroendocrine tumours; cancers of the exocrine glands, such as breast cancer and pancreatic cancer; cancers affecting the thorax, such as pleural and lung cancer; digestive system cancers, such as cancer of the oesophagus, stomach cancer, small bowel cancer, colon cancer and rectal and/or anal cancer; genital cancers, such as prostate cancer, cervical cancer, endometrial cancer, cancer of the vagina and cancer of the vulva; urinary system cancers, such as kidney cancer and bladder cancer; sarcomas, such as soft tissue sarcoma, gastro-intestinal stromal tumours (GIST) and bone sarcoma; skin cancers, such as melanoma; hepatobiliary cancers, such as hepatocellular carcinoma and cholangiocarcinoma, the list being non-limitative.

According to a particularly advantageous embodiment of the invention, the genetically modified human stem cell according to the invention is particularly useful for preventing and/or treating hepatocellular carcinomas and/or associated metastases.

Another aspect of the invention relates to a method for selecting genetically modified stem cells as defined above, characterized in that it comprises the steps of:

a) transducing the human stem cells with a viral vector comprising the exogenous nucleic acid,
b) culturing the human stem cells originating from step a) in a predefined culture medium, and
c) selecting the genetically modified human stem cells expressing the selectable marker gene on their membrane surface.

In a particular embodiment of the invention, the culture medium used is a specific medium for human stem cells, such as the Mesenchymal Stem Cell Growth Medium 2, marketed by Promocell (Product reference: C28009).

Advantageously, the culture medium used comprises 50% of medium having been in contact with the non-transduced human stem cells for 24 hours and 50% fresh of the same medium.

In a particular embodiment, the selectable marker gene is the spliced CD34 gene. Advantageously, the selection of the genetically modified human stem cells expressing the selectable marker gene on their membrane surface is carried out by flow cytometry, in particular by means of the BD-FACS ARIAIII™ appliance, using fluorochrome-coupled anti-CD34 antibodies "Brilliant Violet421™" anti-human CD34 Antibody (Product reference: 343609 from Biolegend).

Another subject of the invention relates to a pharmaceutical composition comprising the genetically modified human stem cell according to the invention as active ingredient and at least one pharmaceutically acceptable excipient. In a particular embodiment of the invention, the pharmaceutical composition according to the invention comprises a therapeutically efficacious quantity of genetically modified human stem cells as active ingredient and at least one pharmaceutically acceptable excipient.

According to a particularly advantageous embodiment of the invention, the pharmaceutical composition comprising a therapeutically efficacious quantity of genetically modified human stem cells as active ingredient and at least one pharmaceutically acceptable excipient as defined above is particularly useful for preventing and/or treating cancer and/or cancer recurrences and/or associated metastases.

Advantageously, the pharmaceutical composition comprising a therapeutically efficacious quantity of genetically modified human stem cells as active ingredient and at least one pharmaceutically acceptable excipient as defined above is administered to a patient suffering from, or suspected of suffering from, cancer and/or cancer recurrences and/or associated metastases.

Advantageously, the cancer is a cancer with solid tumours. By "solid tumour" within the meaning of the present invention, is meant a carcinoma or a sarcoma. In a particular embodiment of the invention, the cancer is a cancer selected from: cancers affecting the central nervous system, such as astrocytomas and gliomas; cancers of the upper aerodigestive tract (ENT), such as cancer of the lips, cancer of the oral cavity, oropharyngeal and nasopharyngeal cancer; cancers of the endocrine glands, such as thyroid cancer, cancer of the adrenal glands and extra-digestive and pulmonary neuroendocrine tumours; cancers of the exocrine glands, such as breast cancer and pancreatic cancer; cancers affecting the thorax, such as pleural and lung cancer; digestive system cancers, such as cancer of the oesophagus, stomach cancer, small bowel cancer, colon cancer and rectal and/or anal cancer; genital cancers, such as prostate cancer, cervical cancer, endometrial cancer, cancer of the vagina and cancer of the vulva; urinary system cancers, such as kidney cancer and bladder cancer; sarcomas, such as soft tissue sarcoma, gastro-intestinal stromal tumours (GIST) and bone sarcoma; skin cancers, such as melanoma; hepatobiliary cancers, such as hepatocellular carcinoma and cholangiocarcinoma, the list being non-limitative.

According to a particularly advantageous embodiment of the invention, the pharmaceutical composition comprising a therapeutically efficacious quantity of genetically modified human stem cells as active ingredient and at least one pharmaceutically acceptable excipient as defined above is particularly useful for preventing and/or treating the solid tumours, and in particular hepatocellular carcinomas, and/or cancer recurrences and/or associated metastases.

Advantageously, the pharmaceutical composition comprising a therapeutically efficacious quantity of genetically modified human stem cells as active ingredient and at least one pharmaceutically acceptable excipient as defined above is administered to a patient suffering from, or suspected of suffering from, solid tumours, and in particular hepatocellular carcinomas, and/or cancer recurrences and/or associated metastases.

In an embodiment, the patient can be a human being, man or woman, regardless of age. In another embodiment, the patient can be a non-human animal, advantageously a non-human mammal, for example a dog, a cat, a mouse, a rat, a hamster, a rabbit, a chinchilla, a horse, a cow, a pig, a sheep, a goat or a primate.

Within the meaning of the present invention, the terms "therapeutically efficacious" or "efficacious quantity for treatment", or "pharmaceutically efficacious" denote the quantity of genetically modified human stem cells necessary to inhibit or reverse a disease, advantageously a cancer, and in particular for treating the solid tumours and particularly hepatocellular carcinomas, and/or associated metastases. The determination of a therapeutically efficacious quantity depends specifically on factors such as the toxicity and efficacy of the medicament. These factors will differ as a function of other factors such as the activity, the relative bioavailability, the body weight of the patient, the severity of the adverse effects and the preferred administration route. The toxicity can be determined by using methods that are well known in the art. The same applies for the efficacy. A pharmaceutically efficacious quantity is consequently a quantity that is considered by the clinician as toxicologically tolerable but efficacious.

The dosage can be adjusted appropriately to achieve the desired medicament levels (for example, of genetically modified human stem cells), local or systemic, in particular transarterial, as a function of the administration route. In the case where a patient's response is insufficient at such doses, higher doses (or more efficacious doses via a different, more localized administration route) can be used to the extent that the patient's tolerance permits. Several injections at approximately one week's interval can also be used to achieve appropriate levels of toxic metabolites formed to elicit the death of the tumour cells and the triggering of an antitumor immune response. "Dose" and "dosage" are used interchangeably herein.

The frequency of injection is linked to the half-life of the genetically modified human stem cells.

In an advantageous embodiment, the pharmaceutical composition according to the invention is administered to the patient at the rate of one administration per week for at least four weeks. Advantageously, the pharmaceutical composition according to the invention is administered to the patient at the rate of two administrations, advantageously three administrations, advantageously four administrations, advantageously five administrations, advantageously six administrations, advantageously seven administrations per week. Advantageously, the pharmaceutical composition according to the invention is administered to the patient for at least four weeks, advantageously at least five weeks, advantageously at least six weeks, advantageously at least seven weeks, advantageously at least eight weeks, advantageously at least nine weeks, advantageously at least ten weeks.

In an advantageous embodiment, the pharmaceutical composition according to the invention also comprises at least a second active ingredient. In a particularly advantageous embodiment of the invention, the at least a second active ingredient can interact synergically with the genetically modified human stem cells according to the invention.

Advantageously, the second active ingredient is an anti-cancer agent. By way of example of second active ingredient, there may be mentioned particularly the cytostatic agents, the cytotoxic agents, the cytoprotective agents, the growth inhibitor agents, the toxins and combinations thereof. Examples of anti-cancer agents capable of being used in tumour therapy with the genetically modified human stem cells of the invention comprise cyclophosphamide (CAS No. 50-18-0, also known as cyclophosphane, and the trade names Endoxan®, Neosar®, Procytox® and Revimmune®), AQ4N (1, 4) -bis- {[2- (dimethylamino-N-oxide) ethyl] amino} 5,8-dihydroxyanthracene-9,10-dione, (also known as Banoxantrone®), Ifosfamide (CAS No. 3778-73-2), Bezyloxyresorufine, 7-Ethoxy-4-trifluoro-methyl-coumarin (EFC), Bupropion, Thiotepa (N,N'N'-triethylenethiophosphoramide, CAS No. 52-24-4), mytomycin C (CAS No. 50-0-07), tirapazamine (SR-4233, CAS No. 27314-97-2). By way of examples of cytoprotective agent, mesna may be mentioned particularly, also known under the trade name of Uromitexan®. Advantageously, the second active ingredient can comprise a combination of anti-cancer agents, such as those listed above. In a particularly advantageous embodiment, the second active ingredient is a combination of an anti-cancer and a cytoprotective agent. In a particularly advantageous embodiment, the second active ingredient is a combination of cyclophosphamide and mesna.

In a particular embodiment, the pharmaceutical composition according to the invention comprises the genetically modified human stem cells as defined above as active ingredient and cyclophosphamide as second active ingredient.

In a particular embodiment, the pharmaceutical composition according to the invention comprises the genetically modified human stem cells as defined above as active ingredient and mesna as second active ingredient.

In a particular embodiment according to the invention, the second active ingredient can be in the form of granules, powders, tablets, coated tablets, (micro)capsules, syrups, emulsions, suspensions or prolonged-release preparations. In another particular embodiment according to the invention, the second active ingredient can be in a form that can be administered via parenteral route.

In a particular embodiment, the pharmaceutical composition according to the invention comprises the genetically modified human stem cells as defined above as active ingredient and cyclophosphamide as second active ingredient and at least one pharmaceutically acceptable excipient.

In a particular embodiment, the pharmaceutical composition according to the invention comprises genetically modified human stem cells as defined above as active ingredient and cyclophosphamide as second active ingredient and at least one pharmaceutically acceptable excipient.

In an advantageous embodiment of the invention, when the pharmaceutical composition comprises a second active ingredient, the pharmaceutical composition is adapted for a simultaneous administration or a sequential administration of the genetically modified human stem cells and of the second active ingredient.

Within the meaning of the present invention, by "simultaneous administration" is meant an administration of the genetically modified human stem cells and of the second active ingredient at the same time, at the same moment, to a patient in therapeutically efficacious quantities in order to permit the synergic effect of the pharmaceutical composition. This does not necessarily mean that the genetically modified human stem cells and the second active ingredient must be administered in the form of a mixture; they can in fact be administered simultaneously but separately, in the form of distinct compositions.

By "present in two distinct compositions" is meant that the genetically modified human stem cells and the second active ingredient are physically separate. They are then implemented, administered separately in therapeutically efficacious quantities, to permit the synergic effect of the pharmaceutical composition, without prior mixing, in several (at least two) dosage forms (for example two distinct compositions).

In another particular embodiment of the invention, the genetically modified human stem cells and the second active ingredient can be present in one and the same composition in therapeutically efficacious quantities in order to permit the synergic effect of the pharmaceutical composition. Within the meaning of the present invention, by "present in one and the same composition" is meant the physical combination of the genetically modified human stem cells and the second active ingredient. The genetically modified human stem cells and the second active ingredient must then be administered simultaneously, as they are administered together in the form of a mixture, in one and the same dosage form (for example in a single composition containing the genetically modified human stem cells and the anti-cancer agent) and in therapeutically efficacious quantities, to permit the synergic effect of the pharmaceutical composition.

Within the meaning of the present invention, by the expression "sequential administration" is meant that the genetically modified human stem cells and the second active ingredient are administered in therapeutically efficacious quantities in order to permit the synergic effect of the pharmaceutical composition, not simultaneously but separately over time, one after another. The terms "precede" or "preceding" and "follow" or "following" then apply. The term "precede" or "preceding" is used when a component of the pharmaceutical composition according to the invention is administered a few minutes or a few hours, or even a few days before the administration of the other component(s) of the pharmaceutical composition. Conversely, the term "follow" or "following" is used when a component of the pharmaceutical composition according to the invention is administered a few minutes or a few hours, or even a few days after the administration of the other component(s) of the pharmaceutical composition. In a particularly advantageous embodiment of the invention, the genetically modified human stem cells are administered several days before the second active ingredient.

In an advantageous embodiment of the invention, when the pharmaceutical composition comprises a second active ingredient, the pharmaceutical composition is adapted for a sequential administration of the genetically modified human stem cells and of the second active ingredient. Advantageously, the second active ingredient is cyclophosphamide used alone or in combination with mesna.

In a particular embodiment of the invention, the genetically modified human stem cells are administered to the patient, then two or three days after the administration of the genetically modified human stem cells, cyclophosphamide, alone or in combination with mesna, is administered to this same patient, at the rate of two administrations of genetically modified human stem cells and of cyclophosphamide, alone or in combination with mesna, per week for at least four weeks, advantageously at least five weeks, advantageously at least six weeks, advantageously at least seven weeks, advantageously at least eight weeks, advantageously at least nine weeks, advantageously at least ten weeks.

As a function of the intended in vivo administration route, the pharmaceutical composition used can be in the solid, semi-solid or liquid dosage form, such as for example tablets, pills, powders, capsules, gels, ointments, liquids, suspensions or similar. Preferably, the pharmaceutical compositions are administered in suitable unitary dosage forms for single administration in precise dosage quantities. The pharmaceutical compositions can also comprise, as a function of the desired formulation, at least one pharmaceutically acceptable support or diluent, which are defined as aqueous-base vehicles currently used for formulations intended for human administration. The diluent is selected so as not to affect the biological activity of the active constituents present in the pharmaceutical composition of the invention. Examples of such diluents are distilled water, physiological serum, Ringer solution, dextrose solution and Hank's solution. Efficacious quantities of such a diluent or support are efficacious quantities for obtaining a pharmaceutically acceptable formulation in terms of solubility of the constituents, biological activity, etc. In certain embodiments, the pharmaceutical constituents herein are sterile.

Suitable pharmaceutical preparation liquid forms can particularly comprise aqueous or saline solutions, said aqueous or saline solutions being able to be micro-encapsulated, notched, applied onto microscopic gold particles, contained in liposomes.

The administration of the pharmaceutical composition or of the genetically modified human stem cell according to the present invention can be carried out via any administration route, including via oral, topical, parenteral (also called systemic or general route), intramuscular, intranasal, sublingual, intratracheal routes, via inhalation, ocular, vaginal and rectal routes. Intracapsular, intravenous, transarterial, intraarterial and intraperitoneal administration routes can also be used. A person skilled in the art will know how to select the appropriate administration route as a function of the disorder to be treated.

Advantageously, the pharmaceutical composition or the genetically modified human stem cell according to the present invention can be administered to a subject via parenteral route, advantageously via transarterial route.

When it is desirable to administer them via systemic route, the compositions can be formulated for parenteral administration by injection, for example by bolus injection or continuous perfusion. The formulations for injection can be presented in a unitary dosage form, for example in ampoules or multiple-dose containers, with an added preservative. The compositions can adopt forms such as suspensions, solutions or emulsions in oily or aqueous vehicles, and can contain formulation agents such as suspension agents, stabilizers and/or dispersants.

The pharmaceutical formulations for parenteral administration comprise aqueous solutions of the active compositions in water-soluble form. In addition, suspensions of the active compositions can be prepared in the form of appropriate suspensions for oily injection. The appropriate lipophilic solvents or vehicles comprise fatty oils such as sesame oil, or synthetic fatty acid esters, such as ethyl oleate or triglycerides, or liposomes. The aqueous suspensions for injection can contain substances that increase the viscosity of the suspension, such as sodium carboxymethylcellulose, sorbitol or dextran. Optionally, the suspension can also contain suitable stabilizers or agents that increase the solubility of the compositions, to permit the preparation of highly concentrated solutions. As a variant, the active compositions can be in the form of powders to be made up with a suitable vehicle, for example pyrogen-free sterile water, before use.

Even more advantageously, the pharmaceutical composition or the genetically modified human stem cell according to the present invention can be administered to a patient via transarterial route. According to a particular embodiment of the invention, the pharmaceutical composition or the genetically modified human stem cell according to the present invention are in a suitable form for administration thereof via transarterial route.

In a particularly advantageous embodiment, the genetically modified human stem cells according to the present invention represent a ratio of 0.5 á 98% by weight, or more, of the total weight of the pharmaceutical composition in question.

In a particularly advantageous embodiment of the present invention, the pharmaceutical composition according to the invention comprises only the genetically modified human stem cells as defined above, as single active ingredient.

Another subject of the invention relates to a method for the preventive treatment of cancer and/or associated metastases, comprising administration to the patient of genetically modified human stem cells or of a pharmaceutical composition comprising a therapeutically efficacious quantity of genetically modified human stem cells as active ingredient and at least one pharmaceutically acceptable excipient as defined above.

Within the meaning of the present invention, the term "prevention" or "prophylaxis" or "preventative treatment" or "prophylactic treatment" comprises a treatment leading to the prevention of a disease as well as a treatment reducing and/or delaying the incidence of a disease or the risk of occurrence of the disease.

According to the present invention, the genetically modified human stem cell is particularly efficacious for preventing recurrences and the appearance of new metastases, by eliciting a strong antitumor immune response, thus inducing a protective effect against recurrences and metastases.

In a particularly advantageous embodiment, the present invention relates to a method for the preventive treatment of cancer and/or cancer recurrences and/or associated metastases, comprising administration to the patient of genetically modified human stem cells or of a pharmaceutical composition comprising a therapeutically efficacious quantity of genetically modified human stem cells as active ingredient and at least one pharmaceutically acceptable excipient as defined above and a second active ingredient as defined above.

Advantageously, the cancer is a cancer with solid tumours. By "solid tumour" within the meaning of the present invention, is meant a carcinoma or a sarcoma. In a particular embodiment of the invention, the cancer is a cancer selected from: cancers affecting the central nervous system, such as astrocytomas and gliomas; cancers of the upper aerodigestive tract (ENT), such as cancer of the lips, cancer of the oral cavity, oropharyngeal and nasopharyngeal cancer; cancers of the endocrine glands, such as thyroid cancer, cancer of the adrenal glands and extra-digestive and pulmonary neuroendocrine tumours; cancers of the exocrine glands, such as breast cancer and pancreatic cancer; cancers affecting the thorax, such as pleural and lung cancer; digestive system cancers, such as cancer of the oesophagus, stomach cancer, small bowel cancer, colon cancer and rectal and/or anal cancer; genital cancers, such as prostate cancer, cervical cancer, endometrial cancer, cancer of the vagina and cancer of the vulva; urinary system cancers, such as kidney cancer and bladder cancer; sarcomas, such as soft tissue sarcoma, gastro-intestinal stromal tumours (GIST) and bone sarcoma; skin cancers, such as melanoma; hepatobiliary cancers, such as hepatocellular carcinoma and cholangiocarcinoma, the list being non-limitative. Advantageously, the cancer is a solid tumour, in particular a hepatocellular carcinoma, and/or cancer recurrences and/or associated metastases.

In a particularly advantageous embodiment, the present invention relates to a method for the preventive treatment of hepatocellular carcinoma, comprising administration to the patient of genetically modified human stem cells or of a pharmaceutical composition comprising a therapeutically efficacious quantity of genetically modified human stem cells as active ingredient and at least one pharmaceutically acceptable excipient as defined above.

In a particularly advantageous embodiment, the present invention relates to a method for the preventive treatment of hepatocellular carcinoma, comprising administration to the patient of genetically modified human stem cells or of a pharmaceutical composition comprising a therapeutically efficacious quantity of genetically modified human stem cells as active ingredient and at least one pharmaceutically acceptable excipient as defined above and a second active ingredient as defined above.

In a particularly advantageous embodiment, the present invention relates to the use of a pharmaceutical composition comprising a therapeutically efficacious quantity of genetically modified human stem cells as active ingredient in the production of a medicament intended for the prevention of cancer and/or cancer recurrences and/or associated metastases.

Advantageously, the cancer is a cancer with solid tumours. By “solid tumour” within the meaning of the present invention, is meant a carcinoma or a sarcoma. In a particular embodiment of the invention, the cancer is a cancer selected from: cancers affecting the central nervous system, such as astrocytomas and gliomas; cancers of the upper aerodigestive tract (ENT), such as cancer of the lips, cancer of the oral cavity, oropharyngeal and nasopharyngeal cancer; cancers of the endocrine glands, such as thyroid cancer, cancer of the adrenal glands and extra-digestive and pulmonary neuroendocrine tumours; cancers of the exocrine glands, such as breast cancer and pancreatic cancer; cancers affecting the thorax, such as pleural and lung cancer; digestive system cancers, such as cancer of the oesophagus, stomach cancer, small bowel cancer, colon cancer and rectal and/or anal cancer; genital cancers, such as prostate cancer, cervical cancer, endometrial cancer, cancer of the vagina and cancer of the vulva; urinary system cancers, such as kidney cancer and bladder cancer; sarcomas, such as soft tissue sarcoma, gastro-intestinal stromal tumours (GIST) and bone sarcoma; skin cancers, such as melanoma; hepatobiliary cancers, such as hepatocellular carcinoma and cholangiocarcinoma, the list being non-limitative. Advantageously, the cancer is a solid tumour, in particular a hepatocellular carcinoma and/or associated metastases.

In a particularly advantageous embodiment, the present invention relates to the use of a pharmaceutical composition comprising a therapeutically efficacious quantity of genetically modified human stem cells as active ingredient in the production of a medicament intended for the prevention of solid tumours, and in particular hepatocellular carcinomas, and/or cancer recurrences and/or associated metastases.

Another subject of the invention relates to a method for the curative treatment of cancer and/or associated metastases in patients requiring an administration, comprising administration to said patients of genetically modified human stem cells or of a pharmaceutical composition comprising a therapeutically efficacious quantity of genetically modified human stem cells as active ingredient and at least one pharmaceutically acceptable excipient as defined above.

Within the meaning of the present invention, the term “treatment” or “curative treatment” is defined as a treatment leading to recovery or treatment that relieves, ameliorates and/or eliminates, reduces and/or stabilizes the symptoms of a disease or the suffering that it elicits.

Another subject of the invention relates to a method for the curative treatment of cancer and/or cancer recurrences and/or associated metastases in patients requiring an administration, comprising administration to said patients of genetically modified human stem cells or of a pharmaceutical composition comprising a therapeutically efficacious quantity of genetically modified human stem cells as active ingredient and at least one pharmaceutically acceptable excipient as defined above and a second active ingredient as defined above.

Advantageously, the cancer is a cancer with solid tumours. By “solid tumour” within the meaning of the present invention, is meant a carcinoma or a sarcoma. In a particular embodiment of the invention, the cancer is a cancer selected from: cancers affecting the central nervous system, such as astrocytomas and gliomas; cancers of the upper aerodigestive tract (ENT), such as cancer of the lips, cancer of the oral cavity, oropharyngeal and nasopharyngeal cancer; cancers of the endocrine glands, such as thyroid cancer, cancer of the adrenal glands and extra-digestive and pulmonary neuroendocrine tumours; cancers of the exocrine glands, such as breast cancer and pancreatic cancer; cancers affecting the thorax, such as pleural and lung cancer; digestive system cancers, such as cancer of the oesophagus, stomach cancer, small bowel cancer, colon cancer and rectal and/or anal cancer; genital cancers, such as prostate cancer, cervical cancer, endometrial cancer, cancer of the vagina and cancer of the vulva; urinary system cancers, such as kidney cancer and bladder cancer; sarcomas, such as soft tissue sarcoma, gastro-intestinal stromal tumours (GIST) and bone sarcoma; skin cancers, such as melanoma; hepatobiliary cancers, such as hepatocellular carcinoma and cholangiocarcinoma, the list being non-limitative. Advantageously, the cancer is a solid tumour, in particular a hepatocellular carcinoma and/or associated metastases.

Another subject of the invention relates to a method for the curative treatment of a solid tumour, advantageously of the hepatocellular carcinomas and/or associated metastases, in patients requiring an administration, comprising administration to said patients of genetically modified human stem cells or of a pharmaceutical composition comprising a therapeutically efficacious quantity of genetically modified human stem cells as active ingredient and at least one pharmaceutically acceptable excipient as defined above.

Another subject of the invention relates to a method for the curative treatment of a solid tumour, advantageously of the hepatocellular carcinomas and/or associated metastases, in patients requiring an administration, comprising administration to said patients of genetically modified human stem cells or of a pharmaceutical composition comprising a therapeutically efficacious quantity of genetically modified human stem cells as active ingredient and at least one pharmaceutically acceptable excipient as defined above and a second active ingredient as defined above. In a particularly advantageous embodiment, the present invention relates to the use of a pharmaceutical composition comprising a therapeutically efficacious quantity of genetically modified human stem cells as active ingredient in the production of a medicament intended for the treatment of cancer and/or of associated metastases.

Advantageously, the cancer is a cancer with solid tumours. By “solid tumour” within the meaning of the present invention, is meant a carcinoma or a sarcoma. In a particular embodiment of the invention, the cancer is a cancer selected from: cancers affecting the central nervous system, such as astrocytomas and gliomas; cancers of the upper aerodigestive tract (ENT), such as cancer of the lips, cancer of the oral cavity, oropharyngeal and nasopharyngeal cancer; cancers of the endocrine glands, such as thyroid cancer, cancer of the adrenal glands and extra-digestive and pulmonary neuroendocrine tumours; cancers of the exocrine glands, such as breast cancer and pancreatic cancer; cancers affecting the thorax, such as pleural and lung cancer; digestive system cancers, such as cancer of the oesophagus, stomach cancer, small bowel cancer, colon cancer and rectal and/or anal cancer; genital cancers, such as prostate cancer, cervical cancer, endometrial cancer, cancer of the vagina and cancer of the vulva; urinary system cancers, such as kidney cancer and bladder cancer; sarcomas, such as soft tissue sarcoma, gastro-intestinal stromal tumours (GIST) and bone sarcoma; skin cancers, such as melanoma; hepatobiliary cancers, such as hepatocellular carcinoma and cholangiocarcinoma, the list being non-limitative.

In a particularly advantageous embodiment, the present invention relates to the use of a pharmaceutical composition comprising a therapeutically efficacious quantity of genetically modified human stem cells as active ingredient in the production of a medicament intended for the treatment of the solid tumours, and in particular hepatocellular carcinomas, and/or associated metastases.

The invention claimed is:

1. An isolated genetically modified human stem cell, in which said human stem cell comprises an exogenous nucleic acid comprising a region coding for a fusion protein comprising a mutant human cytochrome P450 2B6 (CYP2B6*) protein of SEQ ID No. 1; and an NADPH-cytochrome P450 reductase protein of SEQ ID No. 2; functionally bound to a promoter, said exogenous nucleic acid having been inserted into one of the genomic safe harbors of said human stem cell, wherein the exogenous nucleic acid further comprises a selectable marker gene consisting of a spliced CD34 selectable marker gene of sequence SEQ ID No. 5 functionally linked to a nucleic acid of sequence SEQ ID No. 6 coding for the 2A peptide.

2. The isolated genetically modified human stem cell according to claim 1, in which said human stem cell is chosen from mesenchymal stem cells (MSC), induced pluripotent stem cells (iPSC) and induced mesenchymal stem cells (iMSC).

3. The isolated genetically modified human stem cell according to claim 1, in which the genomic safe harbor is selected from: the AAVS1 site on chromosome 19, the CCR5 site on chromosome 3, the hROSA26 site on chromosome 3, the 323 site on chromosome 1, the 325 site on chromosome 8, the 289 site on chromosome 1, the 227 site on chromosome 1, the 229 site on chromosome 2, the 253 site on chromosome 2, the 255 site on chromosome 5, the 257 site on chromosome 7, the 259 site on chromosome 14, the 261 site on chromosome 17, the 263 site on chromosome X, the 317 site on chromosome 2, the 303 site on chromosome 2, the 331 site on chromosome 3, the 283 site on chromosome 4, the 231 site on chromosome 4, the 315 site on chromosome 5, the 327 site on chromosome 5, the 305 site on chromosome 5, the 307 site on chromosome 16, the 309 site on chromosome 20, the 285 site on chromosome 6, the 233 site on chromosome 6, the 311 site on chromosome 6, the 299 site on chromosome 6, the 301 site on chromosome 7, the 293 site on chromosome 8, the 319 site on chromosome 11, the 333 site on chromosome 12, the 295 site on chromosome 12, the 329 site on chromosome 12, the 297 site on chromosome 17, the 291 site on chromosome 22, the 313 site on chromosome X and the 321 site on chromosome X.

4. The isolated genetically modified human stem cell according to claim 1, in which the promoter is an EF1-α promoter.

5. The isolated genetically modified human stem cell according to claim 1, in which the human stem cell was obtained by retroviral transduction with a viral vector comprising the exogenous nucleic acid.

6. A method for obtaining and selecting genetically modified stem cells according to claim 1, which comprises the steps of:

a) transducing the human stem cells with a viral vector comprising an exogenous nucleic acid, said nucleic acid comprising a region coding for a fusion protein comprising a mutant human cytochrome P450 2B6 (CYP2B6*) protein of SEQ ID No. 1; and an NADPH-cytochrome P450 reductase protein of SEQ ID No. 2; functionally bound to a promoter and a selectable marker gene consisting of a spliced CD34 selectable marker gene of sequence SEQ ID No. 5 functionally linked to a nucleic acid of sequence SEQ ID No. 6 coding for the 2A peptide, b) culturing the human stem cells in a predefined culture medium, c) selecting the genetically modified human stem cells expressing the selectable marker gene on their membrane surface.

7. A pharmaceutical composition comprising the genetically modified human stem cell according to claim 1, as active ingredient and at least one pharmaceutically acceptable excipient.

8. The pharmaceutical composition according to claim 7, also comprising cyclophosphamide.

9. The pharmaceutical composition according to claim 8, which is adapted for a sequential administration of the genetically modified human stem cells and cyclophosphamide.

10. A method for inducing a protective effect against cancer recurrences and metastases comprising administering the pharmaceutical composition of claim 7 to a patient.

11. The method of claim 10, wherein the cancer is a solid tumour.

12. An isolated genetically modified human stem cell comprising an exogenous nucleic acid comprising a region coding for a fusion protein comprising a mutant human cytochrome P450 2B6 (CYP2B6*) protein of SEQ ID No. 1; and an NADPH-cytochrome P450 reductase protein of SEQ ID No. 2; functionally bound to a promoter, wherein the exogenous nucleic acid further comprises a selectable marker gene consisting of a spliced CD34 selectable marker gene of sequence SEQ ID No. 5 functionally linked to a nucleic acid of sequence SEQ ID No. 6 coding for the 2A peptide.

13. The isolated genetically modified human stem cell of claim 10, wherein the exogenous nucleic acid is of sequence SEQ ID No. 8.

14. The isolated genetically modified human stem cell according to claim 12, in which said human stem cell is chosen from mesenchymal stem cells (MSC), induced pluripotent stem cells (iPSC) and induced mesenchymal stem cells (iMSC).

15. The isolated genetically modified human stem cell according to claim 12, in which the promoter is an EF1-a promoter.

16. The isolated genetically modified human stem cell according to claim 12, in which the human stem cell was obtained by retroviral transduction with a viral vector comprising the exogenous nucleic acid.

17. A pharmaceutical composition comprising the genetically modified human stem cell according to claim 1, as active ingredient and at least one pharmaceutically acceptable excipient.

18. The pharmaceutical composition according to claim 17, also comprising cyclophosphamide.

19. The pharmaceutical composition according to claim 18, which is adapted for a sequential administration of the genetically modified human stem cells and cyclophosphamide.

20. A method for inducing a protective effect against cancer recurrences and metastases comprising administering the pharmaceutical composition of claim 17 to a patient.

21. The method according to claim 20, wherein the pharmaceutical composition or the genetically modified human stem cell is administered via transarterial route.

* * * * *